US010781460B2

(12) United States Patent
Orishimo et al.

(10) Patent No.: US 10,781,460 B2
(45) Date of Patent: Sep. 22, 2020

(54) DIPHOSPHOMEVALONATE DECARBOXYLASE VARIANT, AND METHOD FOR PRODUCING OLEFIN COMPOUND BY USING THE SAME

(71) Applicants: RIKEN, Wako-shi, Saitama (JP); ZEON CORPORATION, Tokyo (JP); The Yokohama Rubber Co., Ltd., Tokyo (JP)

(72) Inventors: Ryoko Orishimo, Wako (JP); Tomokazu Shirai, Wako (JP); Kazuhiro Takahashi, Tokyo (JP); Misao Hiza, Hiratsuka (JP); Yusuke Tanabe, Hiratsuka (JP)

(73) Assignees: RIKEN, Wako-shi (JP); ZEON CORPORATION, Tokyo (JP); THE YOKOHAMA RUBBER CO., LTD., Tokyo (JP)

( * ) Notice: Subject to any disclaimer, the term of this patent is extended or adjusted under 35 U.S.C. 154(b) by 0 days.

(21) Appl. No.: 15/749,598

(22) PCT Filed: Aug. 3, 2016

(86) PCT No.: PCT/JP2016/072828
§ 371 (c)(1),
(2) Date: Feb. 1, 2018

(87) PCT Pub. No.: WO2017/022804
PCT Pub. Date: Feb. 9, 2017

(65) Prior Publication Data
US 2018/0245104 A1 Aug. 30, 2018

(30) Foreign Application Priority Data

Aug. 3, 2015 (JP) ................................ 2015-153471
Dec. 25, 2015 (JP) ................................ 2015-255317

(51) Int. Cl.
| C12P 7/00 | (2006.01) |
| C12P 7/42 | (2006.01) |
| C12N 9/10 | (2006.01) |
| C12P 5/02 | (2006.01) |
| C12N 9/88 | (2006.01) |
| C12N 15/09 | (2006.01) |
| C12N 5/10 | (2006.01) |
| C12N 15/52 | (2006.01) |

(52) U.S. Cl.
CPC ................ *C12P 5/026* (2013.01); *C12N 5/10* (2013.01); *C12N 9/88* (2013.01); *C12N 15/09* (2013.01); *C12N 15/52* (2013.01); *C12P 5/02* (2013.01); *C12Y 401/01033* (2013.01)

(58) Field of Classification Search
CPC .. C12N 9/88; C12N 9/001; C12Y 401/01033; C12Y 402/03027; C12P 5/026
USPC ................ 435/167, 232, 243, 189, 196, 135
See application file for complete search history.

(56) References Cited

U.S. PATENT DOCUMENTS

| 2007/0077616 A1 | 4/2007 | Keasling et al. |
| 2014/0141482 A1 | 5/2014 | Pearlman et al. |
| 2014/0370564 A1 | 12/2014 | Garcez Lopes et al. |
| 2014/0370565 A1 | 12/2014 | Marliere |
| 2015/0037860 A1 | 2/2015 | Botes et al. |
| 2016/0002672 A1 | 1/2016 | Beck et al. |
| 2016/0160204 A1 | 6/2016 | Mazaleyrat et al. |

FOREIGN PATENT DOCUMENTS

| JP | 2015-501659 A | 1/2015 |
| JP | 2015-501660 A | 1/2015 |
| JP | 2015-519083 A | 7/2015 |
| WO | 2013/092567 A2 | 6/2013 |
| WO | 2014/015210 A2 | 1/2014 |
| WO | 2014/100726 A2 | 6/2014 |
| WO | 2015/004211 A2 | 1/2015 |
| WO | 2015/021045 A2 | 2/2015 |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Oct. 11, 2016 International Search Report issued in International Patent Application No. PCT/JP2016/072828.
Gogerty DS et al., "Formation of isobutene from 3-hydroxy-3-methylbutyrate by diphosphomevalonate decarboxylase." Appl. Environ. Microbiol., vol. 76, No. 24, pp. 8004-8010, 2010.
Ryoko Orishimo et al., "Yuyo Koso no Kishitsu Tokuisei Kaihen to Bio-isoprene Seisan eno Oyo", Proceedings of the Annual Meeting of Japan Society for Bioscience, Biotechnology, and Agrochemistry, vol. 2016, 2016.
Feb. 6, 2018 International Preliminary Report on Patentability issued in International Patent Application No. PCT/JP2016/072828.
Dec. 4, 2018 Extended Search Report issued in European Patent Application No. 16833083.5.

* cited by examiner

*Primary Examiner* — Robert B Mondesi
*Assistant Examiner* — Mohammad Y Meah
(74) *Attorney, Agent, or Firm* — Oliff PLC

(57) ABSTRACT

A method which enables olefin compound production with a high productivity and an enzyme used in the method, a mutation involving amino acid substitution has been introduced into various sites of diphosphomevalonate decarboxylase (MVD), thus preparing a large number of MVD variants. Next, the result of evaluating the variants for the catalytic activity related to the production of olefin compounds such as isoprene has revealed that MVD whose threonine at position 209 is substituted with a different amino acid has the catalytic activity, and that MVD whose arginine at position 74 is further substituted with a different amino acid in addition to position 209 has the catalytic activity at higher levels.

6 Claims, 9 Drawing Sheets

Specification includes a Sequence Listing.

DIPHOSPHOMEVALONATE DECARBOXYLASE VARIANT, AND METHOD FOR PRODUCING OLEFIN COMPOUND BY USING THE SAME

TECHNICAL FIELD

The present invention relates to a method for producing an olefin compound by using a diphosphomevalonate decarboxylase variant. In addition, the present invention relates to the variant, and a method for producing the variant. Further, the present invention also relates to a DNA encoding the variant, and a vector comprising the DNA inserted therein. Moreover, the present invention relates to a method for producing an olefin compound by using a host cell comprising the DNA or the vector introduced therein. Furthermore, the present invention also relates to an agent for promoting olefin compound production, the agent comprising the variant, the DNA, or the vector.

BACKGROUND ART

Olefin compounds such as isoprene and isobutene are quite useful as raw materials of various synthetic polymers such as synthetic rubbers. The compounds can be obtained by chemical methods such as fractional distillation of petroleum.

Nevertheless, even by such chemical methods, the yield is low, the production cost is high, and it takes time. Further, in consideration of the recent environmental problems, there are demands for the development of environmentally-friendly and sustainable methods for producing olefin compounds without wasting limited resources, instead of the chemical methods.

In view of such a situation, efforts have been made to produce olefin compounds by utilizing or modifying metabolic pathways of microorganisms and so forth. For example, there have been disclosed methods for producing isoprene, isobutene, and the like by introducing a mutation into a diphosphomevalonate decarboxylase or the like involved in the mevalonate pathway to utilize the enzyme variant (PTLs 1 to 3).

CITATION LIST

Patent Literatures

[PTL 1] International Publication No. WO2013/092567
[PTL 2] International Publication No. WO2015/004211
[PTL 3] International Publication No. WO2015/021045

SUMMARY OF INVENTION

Technical Problem

The present invention has been made in view of the above-described problems of the conventional techniques. An object of the present invention is to provide an enzyme which enables olefin compound production with a high productivity.

Solution to Problem

In order to achieve the above object, the present inventors first have arrived at an idea that isopentenyl diphosphate production (see the following equation) which uses 5-diphosphomevalonic acid as a substrate, and in which diphosphomevalonate decarboxylase is involved, is applied to the production of olefin compounds such as isoprene.

[Chem. 1]

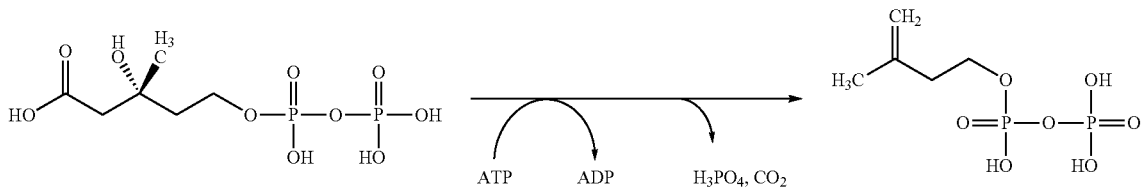

To be more specific, the inventors have arrived at the productions of isoprene and the like via a reaction as represented by the following equation, by introducing a mutation into an amino acid of diphosphomevalonate decarboxylase, and changing the substrate specificity of the enzyme (diphosphomevalonate decarboxylase variant) from the original 5-diphosphomevalonic acid to 3-hydroxy-3-methylpent-4-enotate or the like.

[Chem. 2]

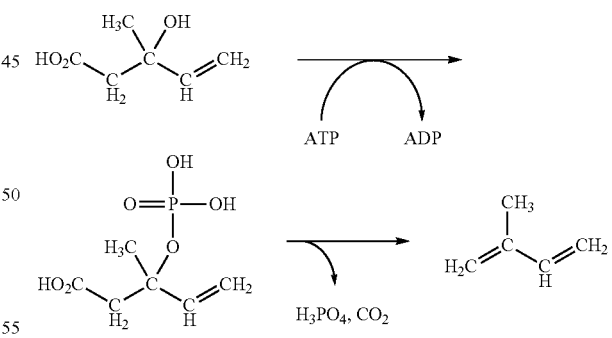

Accordingly, the present inventors introduced a mutation involving amino acid substitution into various sites of diphosphomevalonate decarboxylase, and prepared a large number of diphosphomevalonate decarboxylase variants. Next, these variants were evaluated for the catalytic activity related to isopentenyl diphosphate production using 5-diphosphomevalonic acid as a substrate, and the catalytic activity related to isoprene production using 3-hydroxy-3-methylpent-4-enotate as a substrate.

The result has revealed that introducing the mutation into diphosphomevalonate decarboxylase generally reduces the substrate specificity to 5-diphosphomevalonic acid thereof. Particularly, a diphosphomevalonate decarboxylase whose threonine at position 209 is substituted with a different amino acid (such as serine, arginine, histidine) was found to have a catalytic activity for producing isoprene.

Further, it has been revealed that a diphosphomevalonate decarboxylase (R74HT209R) whose arginine at position 74 is substituted with histidine and whose threonine at position 209 is substituted with arginine exhibits a conspicuously very high catalytic activity related to isoprene production. More concretely, introducing the double mutation into diphosphomevalonate decarboxylase made the catalytic activity related to isopentenyl diphosphate production approximately ⅓ of that of the wild type; meanwhile, the catalytic activity related to isoprene production was enhanced approximately 60 to 80 times as high as that of the wild type. Additionally, the catalytic activity related to isoprene production was remarkably high in comparison with the other variants as shown in FIGS. 3B and 4B to be described later.

Moreover, R74HT209R was evaluated also for the catalytic activity related to the production of another olefin compound (isobutene). As a result, a very high catalytic activity related to isobutene production in comparison with the wild type was found as in the case of the isoprene production.

In addition, it has also been verified that position 74 and position 209 in diphosphomevalonate decarboxylase are not limited to arginine and threonine, respectively, and that even if the amino acids are substituted with different amino acids (at position 74, methionine, histidine, glutamine, lysine, or the like; at position 209, arginine, aspartic acid, glutamic acid, glycine, alanine, or the like), high catalytic activities in the catalytic reaction for isoprene production are generally exhibited in comparison with the wild type.

Further, the catalytic activity for isoprene production of R74HT209R described above was compared with that of a diphosphomevalonate decarboxylase variant (R74MT209R) whose arginine at position 74 is substituted with methionine and whose threonine at position 209 is substituted with arginine. The result has also verified that R74MT209R exhibits the catalytic activity even 1.28 times as high as that of R74HT209R.

Furthermore, it has also been verified that R74MT209R exhibits a high catalytic activity for isobutene production, too. Moreover, it has been verified that R74MT209R has a higher catalytic activity for isobutene production than R74HT209R as in the case of the isoprene production. These have led to the completion of the present invention. Accordingly, the present invention provides the following.

<1> A method for producing an olefin compound, the method comprising the step of reacting ATP and a compound represented by the following formula (1) in presence of a diphosphomevalonate decarboxylase whose threonine at position 209 of an amino acid sequence shown in SEQ ID NO: 2 or threonine corresponding to the position is mutated to a different amino acid

[Chem. 3]

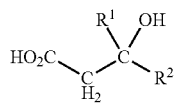

(1)

[in the formula (1), $R^1$ and $R^2$ each independently represent a hydrogen atom, an alkyl group having 1 to 10 carbon atoms, an alkenyl group having 2 to 15 carbon atoms, an aryl group having 6 to 20 carbon atoms, or a halogen atom (the alkyl group and the alkenyl group may be each independently optionally substituted with a hydroxy group and/or a carboxy group)].

<2> A method for producing an olefin compound, the method comprising the steps of:
culturing a host cell comprising
    a DNA encoding a diphosphomevalonate decarboxylase whose threonine at position 209 of an amino acid sequence shown in SEQ ID NO: 2 or threonine corresponding to the position is mutated to a different amino acid or
    a vector comprising the DNA; and
collecting an olefin compound produced in the host cell and/or a culture thereof.

<3> The production method according to <1> or <2>, wherein, in the diphosphomevalonate decarboxylase, the different amino acid mutated from the threonine at position 209 of the amino acid sequence shown in SEQ ID NO: 2 or the threonine corresponding to the position is arginine, aspartic acid, glutamic acid, glycine, alanine, serine, or histidine.

<4> The production method according to any one of <1> to <3>, wherein, in the diphosphomevalonate decarboxylase, arginine at position 74 of the amino acid sequence shown in SEQ ID NO: 2 or arginine corresponding to the position is further mutated to a different amino acid.

<5> The production method according to <4>, wherein,
in the diphosphomevalonate decarboxylase,
    the different amino acid mutated from the threonine at position 209 of the amino acid sequence shown in SEQ ID NO: 2 or the threonine corresponding to the position is arginine, aspartic acid, glutamic acid, glycine, or alanine, and
    the different amino acid mutated from the arginine at position 74 of the amino acid sequence shown in SEQ ID NO: 2 or the arginine corresponding to the position is methionine, histidine, glutamine, or lysine.

<6> The production method according to any one of <1> to <5>, wherein the olefin compound is isoprene.

<7> The production method according to any one of <1> to <5>, wherein the olefin compound is butadiene.

<8> A method for producing a diphosphomevalonate decarboxylase having an enhanced catalytic activity for producing an olefin compound, the method comprising the step of mutating threonine at position 209 of an amino acid sequence shown in SEQ ID NO: 2 or threonine corresponding to the position in a diphosphomevalonate decarboxylase to a different amino acid.

<9> The production method according to <8>, wherein, in the diphosphomevalonate decarboxylase, the different amino acid mutated from the threonine at position 209 of the amino acid sequence shown in SEQ ID NO: 2 or the threonine corresponding to the position is arginine, aspartic acid, glutamic acid, glycine, alanine, serine, or histidine.

<10> The production method according to <8> or <9>, further comprising a step of mutating arginine at position 74 of the amino acid sequence shown in SEQ ID NO: 2 or arginine corresponding to the position in the diphosphomevalonate decarboxylase to a different amino acid.

<11> The production method according to <10>, wherein, in the diphosphomevalonate decarboxylase, the different amino acid mutated from the threonine at position 209 of the amino acid sequence shown in SEQ ID NO: 2 or the threonine corresponding to the position is arginine, aspartic acid, glutamic acid, glycine, or alanine, and the different amino acid mutated from the arginine at position 74 of the amino acid sequence shown in SEQ ID NO: 2 or the arginine corresponding to the position is methionine, histidine, glutamine, or lysine.

<12> The production method according to any one of <8> to <11>, wherein the olefin compound is isoprene.

<13> The production method according to any one of <8> to <11>, wherein the olefin compound is butadiene.

<14> A diphosphomevalonate decarboxylase whose threonine at position 209 of an amino acid sequence shown in SEQ ID NO: 2 or threonine corresponding to the position is mutated to a different amino acid.

<15> The diphosphomevalonate decarboxylase according to <14>, wherein the different amino acid mutated from the threonine at position 209 of the amino acid sequence shown in SEQ ID NO: 2 or the threonine corresponding to the position isarginine, asparticacid, glutamicacid, glycine, alanine, serine, or histidine.

<16> The diphosphomevalonate decarboxylase according to <14> or <15>, wherein arginine at position 74 of the amino acid sequence shown in SEQ ID NO: 2 or arginine corresponding to the position is further mutated to a different amino acid.

<17> The diphosphomevalonate decarboxylase according to <16>, wherein, the different amino acid mutated from the threonine at position 209 of the amino acid sequence shown in SEQ ID NO: 2 or the threonine corresponding to the position is arginine, aspartic acid, glutamic acid, glycine, or alanine, and the different amino acid mutated from the arginine at position 74 of the amino acid sequence shown in SEQ ID NO: 2 or the arginine corresponding to the position is methionine, histidine, glutamine, or lysine.

<18> A DNA encoding the diphosphomevalonate decarboxylase according to any one of <14> to <17>.

<19> A vector comprising the DNA according to <18>.

<20> A host cell comprising the DNA according to <18> or the vector according to <19>.

<21> A method for producing a diphosphomevalonate decarboxylase variant, the method comprising the steps of:

culturing the host cell according to <20>; and collecting a protein expressed in the host cell. <22> An agent for promoting olefin compound production by reacting ATP and a compound represented by the following formula (1), the agent comprising the diphosphomevalonate decarboxylase according to any one of <14> to <17>, a DNA encoding the diphosphomevalonate decarboxylase, or a vector comprising the DNA inserted therein

[Chem. 4]

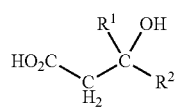

(1)

[in the formula (1), R¹ and R² each independently represent a hydrogen atom, an alkyl group having 1 to 10 carbon atoms, an alkenyl group having 2 to 15 carbon atoms, an aryl group having 6 to 20 carbon atoms, or a halogen atom (the alkyl group and the alkenyl group may be each independently optionally substituted with a hydroxy group and/or a carboxy group)].

<23> The agent according to <22>, wherein the olefin compound is isoprene.

<24> The agent according to <22>, wherein the olefin compound is butadiene.

Advantageous Effects of Invention

The present invention makes it possible to provide an enzyme enabling olefin compound production with a high productivity, and a method for producing an olefin compound by using the enzyme.

represents the analysis results of amino acid-substituted S120C, T46D, S121C, S153A, T209C, T209Q, T209E, T209A, T209Y, T209D, T75I, T209N, N28R, N28E, S153C, N28W, S108T, N28H, L63Q, G154I, G154L, S108C, S108D, N110M, N110Q, S108N, N110I, G154M, G154W, K22Y, T46C, R74W, L61E, L63E, R74Y, L63N, N110E, T48S, T46V, G154F, A119C, A122C, G154E, K22F, A123S, K22R, and K22W.

Figure 3A:
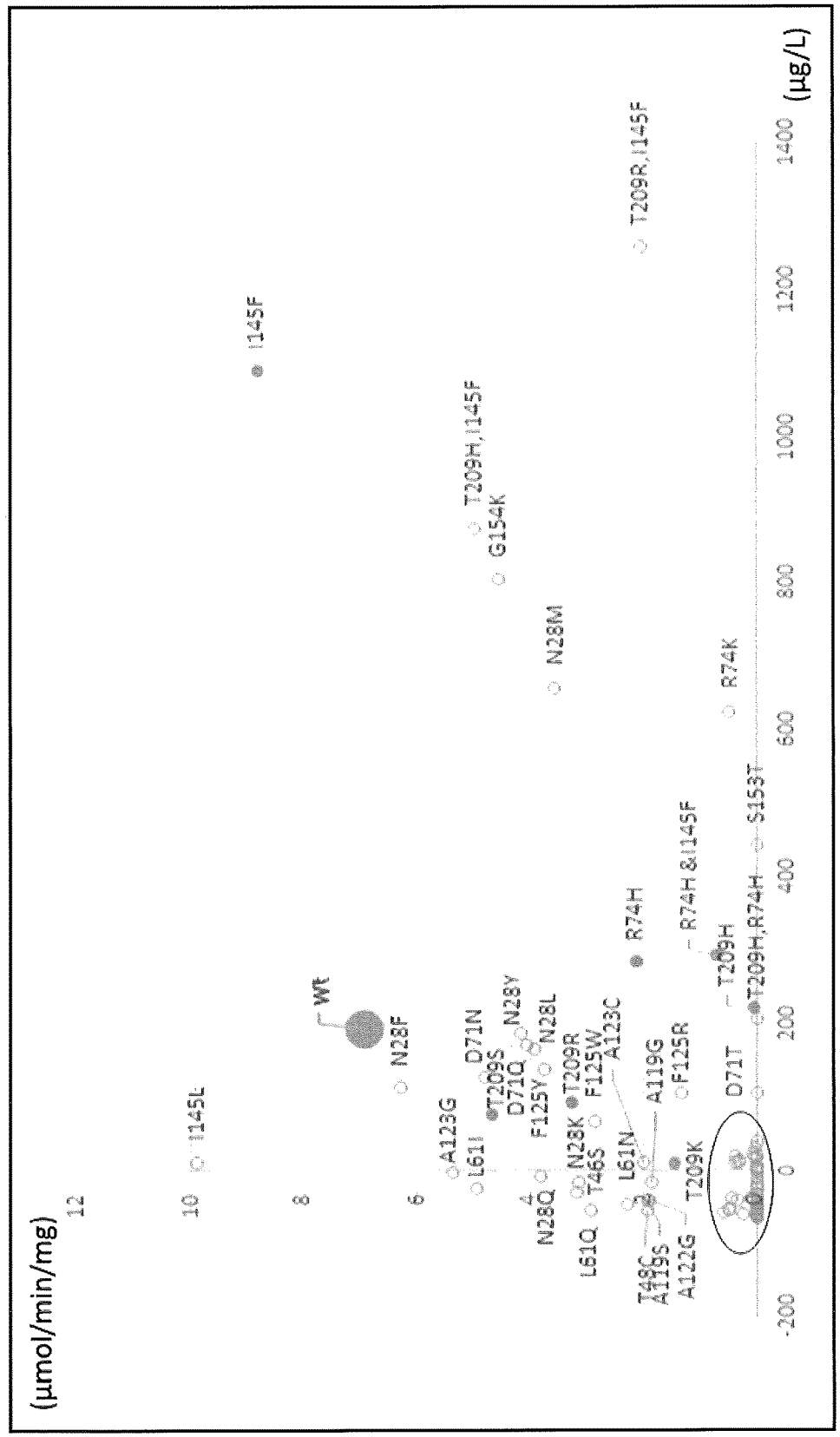
FIG. 3A is a plot showing the result of analyzing the diphosphomevalonate decarboxylase (in the drawing, indicated by "Wt") and variants thereof for the enzymatic activity related to isopentenyl diphosphate production using 5-diphosphomevalonic acid as a substrate (in the drawing, shown on the vertical axis) and the enzymatic activity related to isoprene production using 3-hydroxy-3-methylpent-4-enotate as a substrate (in the drawing, shown on the horizontal axis), the horizontal axis showing the result up to 1400 μg/L. Note that, in FIG. 3A and the following drawings, "T209R, I145F" and the like represent the analysis results of amino acid-substituted diphosphomevalonate decarboxylases; the numbers therein each represent a position (such as position 145, position 209) of the enzyme where a mutation involving amino acid substitution was introduced; an alphabet at the left side of the number represents an amino acid (such as T/threonine, I/isoleucine) before the substitution; and an alphabet at the right side of the number represents an amino acid (such as R/arginine, F/phenylalanine) after the substitution. Moreover, in the drawing, a group of points crowding near the intersection between the vertical axis and the horizontal axis (in the drawing, the group of points is surrounded by the ellipse)
Figure 3B:
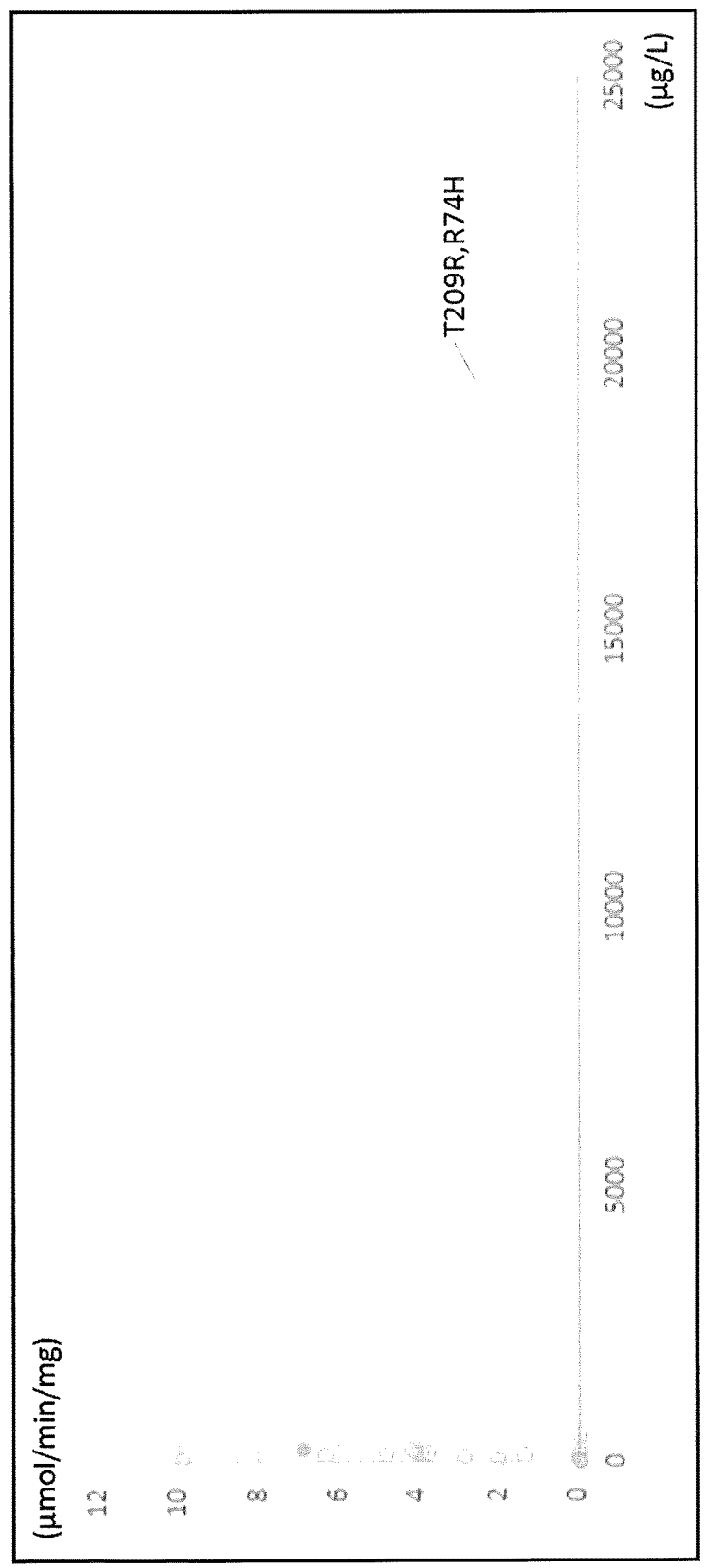

FIG. 3B is a plot showing the result of analyzing the diphosphomevalonate decarboxylase and the variants thereof for the enzymatic activity related to isopentenyl diphosphate production using 5-diphosphomevalonic acid as a substrate (in the drawing, shown on the vertical axis) and the enzymatic activity related to isoprene production using 3-hydroxy-3-methylpent-4-enotate as a substrate (in the drawing, shown on the horizontal axis), the horizontal axis showing the result up to 25000 µg/L.

Figure 4A:
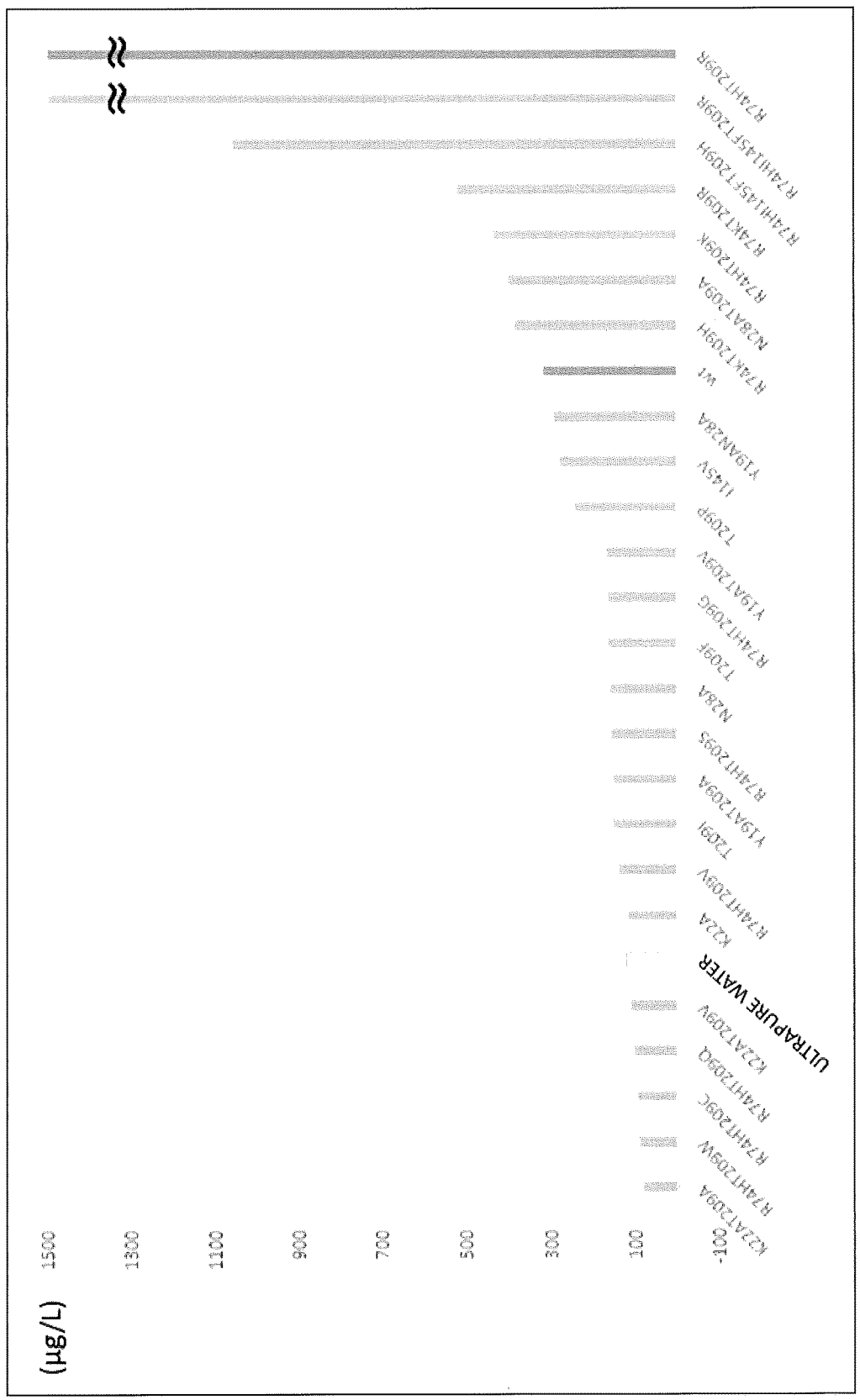

FIG. 4A is a graph showing the result of analyzing the diphosphomevalonate decarboxylase and the variants thereof for the enzymatic activity related to isoprene production using 3-hydroxy-3-methylpent-4-enotate as a substrate up to 1500 g/L. Note that, in FIGS. 4A and B, "ultrapure water" indicates the analysis result (negative control) obtained by using milliQ(registered trademark) water in place of the diphosphomevalonate decarboxylases.

Figure 4B:

FIG. 4B is a graph showing the result of analyzing the diphosphomevalonate decarboxylase and the variants thereof for the enzymatic activity related to isoprene production using 3-hydroxy-3-methylpent-4-enotate as a substrate up to 30000 µg/L.

Figure 5:
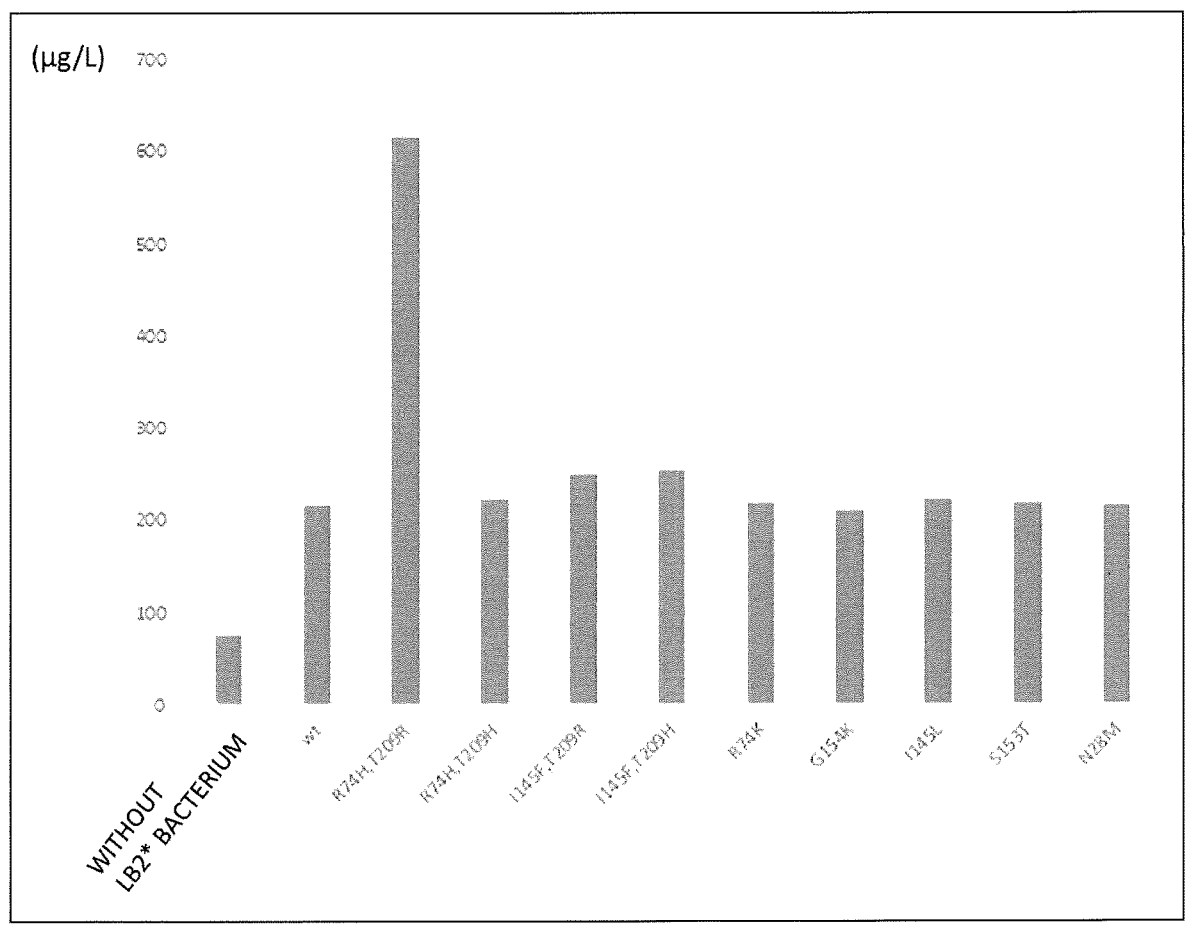

FIG. 5 is a graph showing the result of measuring the amounts of isoprene produced by culturing: *Escherichia coli* which was forced to express a diphosphomevalonate decarboxylase, and a number of *Escherichia coli* which were forced to express the variants. Note that, in the drawing, "LB2*without bacterium" indicates the result of analyzing a sample containing only an LB medium, a substrate, and IPTG as a negative control experiment.

Figure 6A:
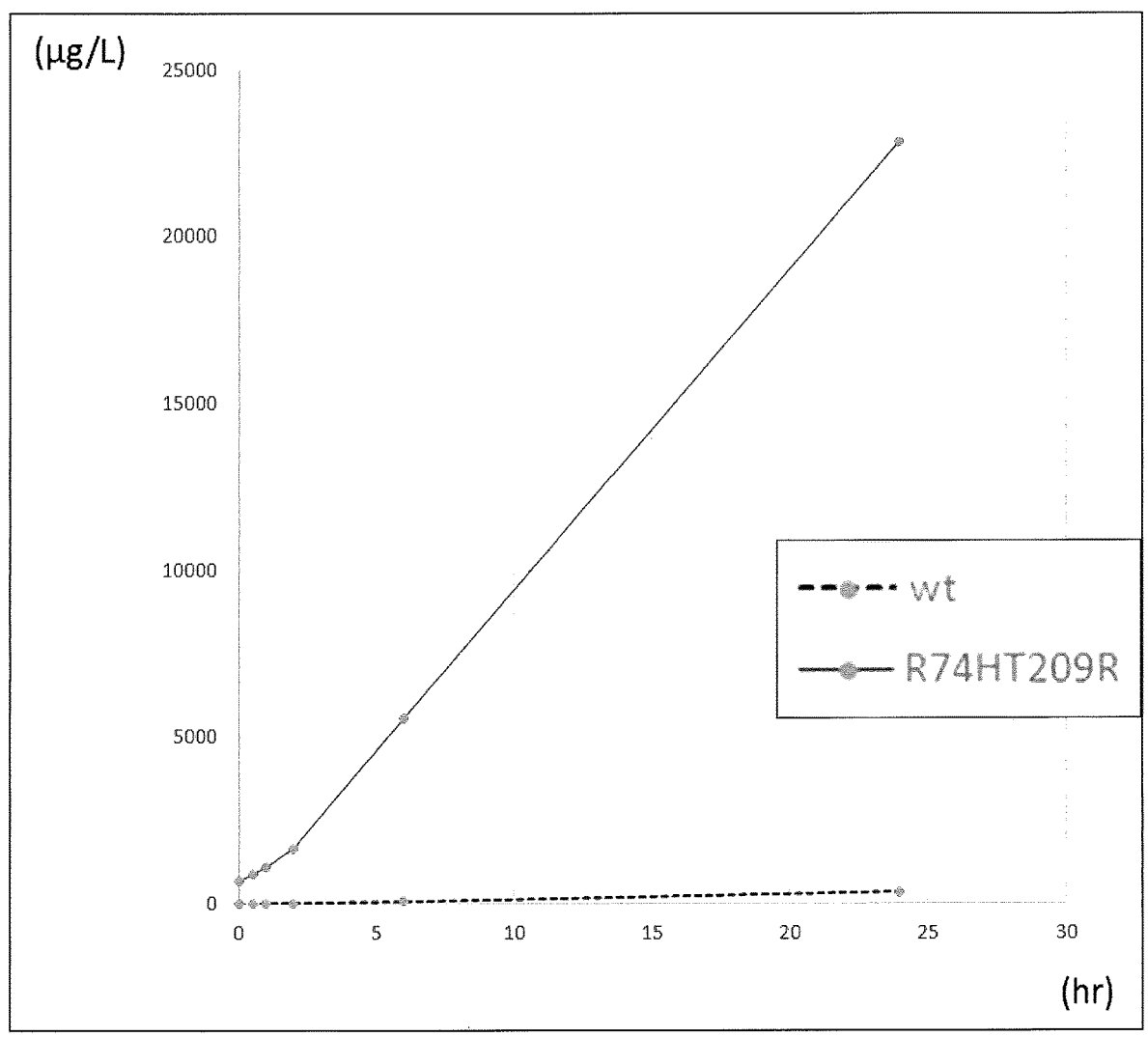

FIG. 6A is a graph showing the change over time in the amount of isoprene synthesized in the presence of: a diphosphomevalonate decarboxylase whose arginine at position 74 was substituted with histidine and threonine at position 209 was substituted with arginine (in the drawing, indicated by "R74HT209R"); or a diphosphomevalonate decarboxylase. The vertical axis represents the amount of isoprene synthesized, and the horizontal axis represents the reaction time.

Figure 6B:
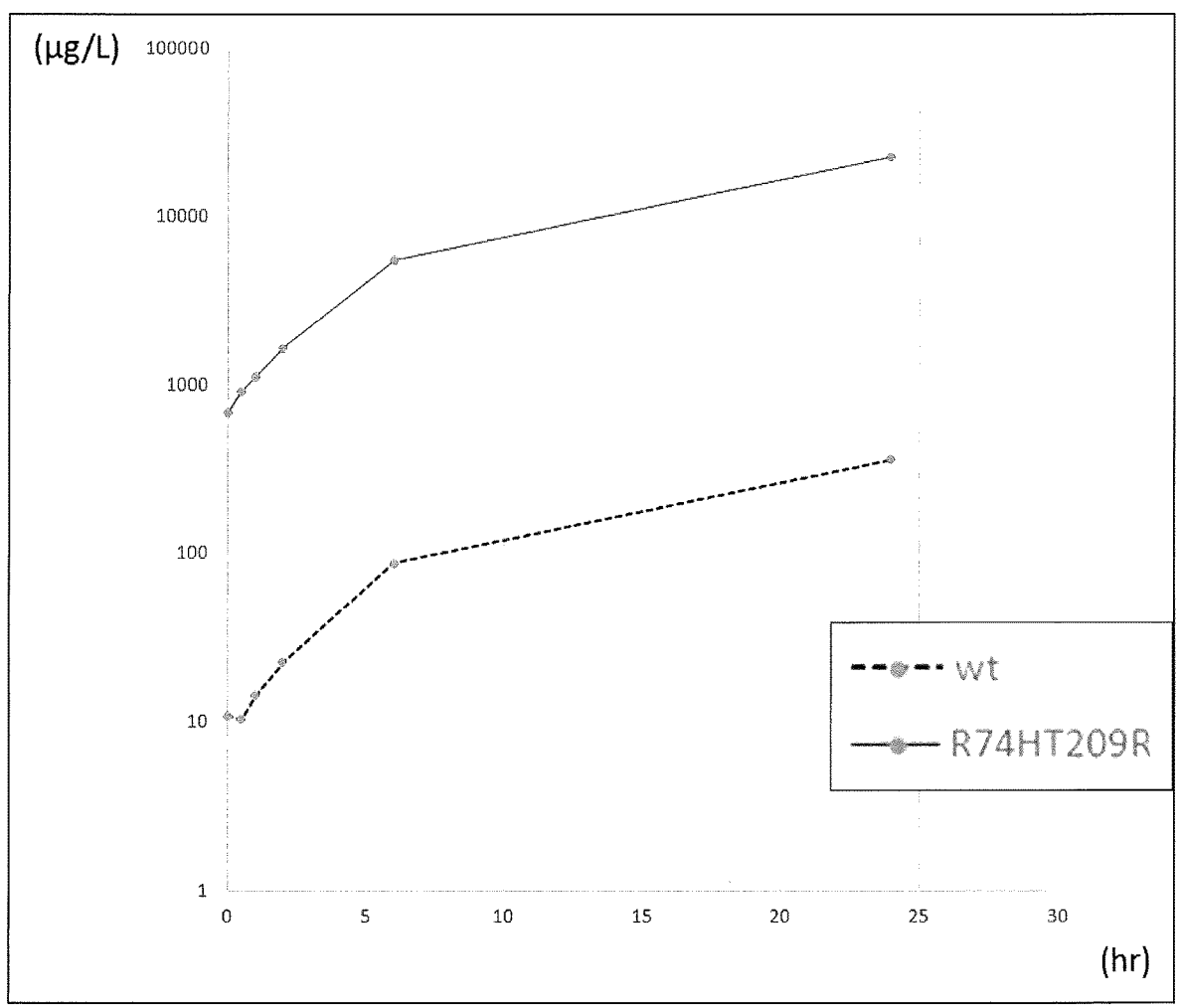

FIG. 6B is a graph obtained by converting the vertical axis of FIG. 6A into the logarithmic representation.

DESCRIPTION OF EMBODIMENTS

<Method 1 for Producing Olefin Compound>

As will be described in Examples later, substituting threonine at position 209 of a diphosphomevalonate decarboxylase with a different amino acid reduces the substrate specificity of the enzyme to the original substrate 5-diphosphomevalonic acid. Moreover, it has been found out that such a diphosphomevalonate decarboxylase variant has a catalytic activity for promoting the following reaction of producing an olefin compound (also referred to as "catalytic activity for producing an olefin compound").

[Chem. 5]

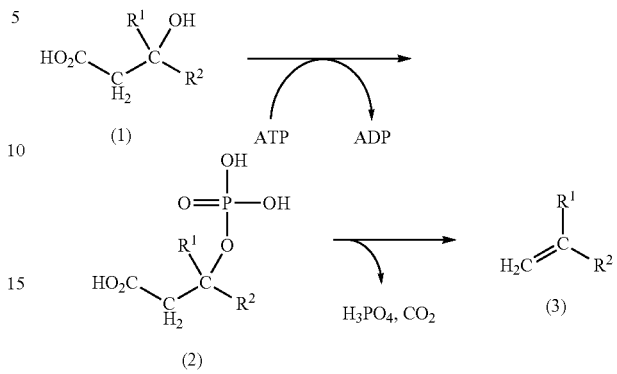

Thus, the present invention provides a method for producing an olefin compound, the method comprising the step of reacting ATP (adenosine triphosphate) and a compound represented by the formula (1) in presence of a diphosphomevalonate decarboxylase whose threonine at position 209 of an amino acid sequence shown in SEQ ID NO: 2 or threonine corresponding to the position (hereinafter, also referred to simply as "threonine at position 209") is mutated to a different amino acid (hereinafter, this diphosphomevalonate decarboxylase will also be referred to as "diphosphomevalonate decarboxylase variant").

In the present invention, the term "olefin compound" means a hydrocarbon compound having at least one carbon-carbon double bond, and may have a substituent such as a hydroxy group and/or a carboxy group, and an atom such as a halogen atom introduced in the compound. Examples of such a compound include monoolefin compounds such as isobutene, ethene, propene, 2-methyl-1-butene, isoprenol, and 3-hydroxy-3-methyl-4-pentenoic acid; and diolefin compounds such as conjugated diene compounds including isoprene, butadiene (1,3-butadiene), piperylene, 2,3-dimethylbutadiene, 1,3-hexadiene, 2-methyl-1,3-pentadiene, chloroprene, and 3-methyl-2,4-pentadienoic acid.

In the compound represented by the following formula (1) which serves as a raw material for producing the olefin compound in the present invention, $R^1$ and $R^2$ are not particularly limited, and each independently represent a hydrogen atom, an alkyl group having 1 to 10 carbon atoms, an alkenyl group having 2 to 15 carbon atoms, an aryl group having 6 to 20 carbon atoms, or a halogen atom (the alkyl group and the alkenyl group may be each independently optionally substituted with a hydroxy group and/or a carboxy group).

[Chem. 6]

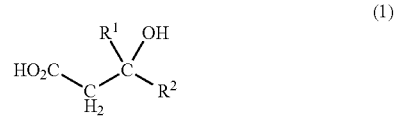

Moreover, in the present invention, in the case where a conjugated diene compound is produced, a compound represented by the following formula (4) is suitably used as a more concrete embodiment of the compound represented by the formula (1), as represented by the following reaction equation.

[Chem. 7]

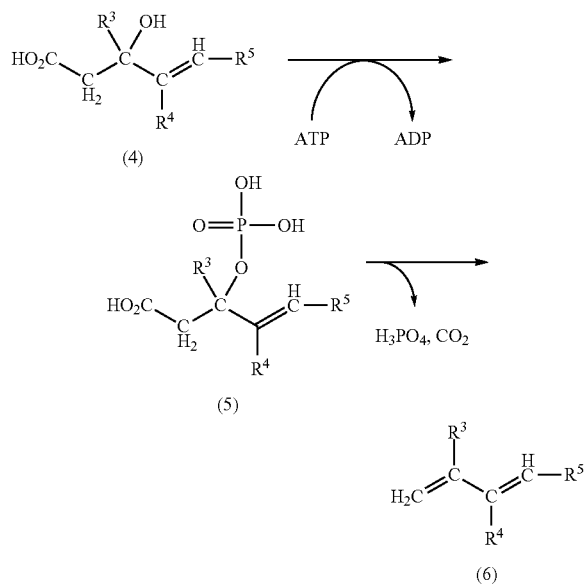

In the compound represented by the formula (4), $R^3$, $R^4$, and $R^5$ are not particularly limited, and each independently represent a hydrogen atom or a substituent selected from the group consisting of an alkyl group having 1 to 10 carbon atoms, a halogen atom, an alkenyl group having 2 to 15 carbon atoms, and an aryl group having 6 to 20 carbon atoms.

In addition, in the present invention, examples of the alkyl group having 1 to 10 carbon atoms include a methyl group, an ethyl group, a n-propyl group, an i-propyl group, an-butyl group, an i-butyl group, a s-butyl group, a t-butyl group, a n-pentyl group, a n-hexyl group, a cyclopropyl group, a cyclopentyl group, a cyclohexyl group, a n-heptyl group, a n-octyl group, a n-decyl group, a (cyclohexyl)methyl group, a (1-methylcyclohexyl)methyl group, a (1-methylcyclopentyl)methyl group, and a (1-ethylcyclohexyl)methyl group. Moreover, examples of the alkenyl group having 2 to 15 carbon atoms include a vinyl group, a 1-propenyl group, a 2-propenyl group, a 2-methyl-2-propenyl group, a 3-butenyl group, a 5-hexenyl group, and a 7-octenyl group. Examples of the aryl group having 6 to 20 carbon atoms include a phenyl group, a 1-naphthyl group, a 2-naphthyl group, an acenaphthyl group, a phenanthryl group, and an anthryl group. Further, the halogen atom is represented by a chlorine atom, a fluorine atom, a bromine atom, or an iodine atom.

Such compounds represented by the formula (1) can be purchased as commercially available products as will be described in Examples later. Alternatively, those skilled in the art can also synthesize the compounds as appropriate with reference to known synthesis methods (for example, the method described in Tetrahedron Letters, 1988, vol. 20, iss. 15, pp. 1763 to 1766).

In the presence of the diphosphomevalonate decarboxylase variant which will be described later, the reaction conditions for ATP and the compound represented by the formula (1) should be conditions under which the reaction is promoted and an olefin compound is produced. Those skilled in the art can adjust and set the composition of a reaction liquid, the pH of the reaction liquid, the reaction temperature, the reaction time, and so forth as appropriate.

For example, the reaction liquid to which the diphosphomevalonate decarboxylase variant, the compound represented by the formula (1) serving as the substrate of the variant, and ATP are added should contain magnesium ions, which serve as a cofactor of the diphosphomevalonate decarboxylase, in an amount of normally 1 to 50 mM, preferably 5 to 20 mM. The other composition and pH are not particularly limited as described above, as long as the reaction is not inhibited. Preferable is a buffer having a pH of 7 to 8, and more preferable is a Tris-HCl buffer having a pH of 7 to 8.

Moreover, the reaction temperature is not particularly limited, either, as long as the reaction is not inhibited. Nevertheless, the reaction temperature is normally 20 to 40° C., and preferably 25 to 37° C. Further, the reaction time should be a time in which an olefin compound can be produced, and is not particularly limited. The reaction time is normally 30 minutes to 7 days, and preferably 12 hours to 2 days.

Furthermore, olefin compounds produced under such conditions generally vaporize readily. Hence, olefin compounds can be collected by known volatile gas recovery and purification methods. The collection method includes gas stripping, fractional distillation, adsorption, desorption, pervaporation, heat or vacuum desorption of isoprene from a solid phase to which the isoprene has been adsorbed, extraction with a solvent, chromatography (for example, gas chromatography), and the like. Moreover, even in a case where the produced olefin compound is a liquid, the olefin compound can be collected by utilizing known recovery and purification methods (such as distillation, chromatography) as appropriate. Further, these methods may be performed alone, or may be performed in an appropriate combination in multiple stages.

<Method 2 for Producing Olefin Compound>

Additionally, as will be described in Examples later, culturing a host cell transformed to express a diphosphomevalonate decarboxylase whose threonine at position 209 of an amino acid sequence shown in SEQ ID NO: 2 or threonine corresponding to the position is mutated to a different amino acid enables olefin compound production with a high productivity. Thus, the present invention also provides a method for producing an olefin compound, the method comprising the steps of:

culturing a host cell comprising a vector or a DNA encoding a diphosphomevalonate decarboxylase variant to be described later; and collecting an olefin compound produced in the host cell and/or a culture thereof.

Although the culturing conditions of the host cell will be described later, a medium therefor is preferably supplemented with the compound represented by the formula (1) which serves as a substrate of the diphosphomevalonate decarboxylase, or magnesium ions which serve as a cofactor, and more preferably supplemented with all of these compounds. In addition, the culturing temperature can be designed and changed as appropriate in accordance with the type of the host cell used, and is normally 20 to 40° C., and preferably 25 to 37° C.

Moreover, in the present invention, the "culture" refers to a medium containing the proliferated host cell, a secretion of the host cell, and a metabolite of the host cell, and the like, the medium obtained by culturing the host cell in a medium. The culture also includes a dilution and a concentrate of these.

From such a host cell and/or culture, an olefin compound is collected without particular limitation, and the above-described known recovery and purification methods can be employed. Further, the collection timing is adjusted as appropriate in accordance with the type of the host cell used, and should be a time in which an olefin compound can be produced. The time is normally 30 minutes to 7 days, and preferably 12 hours to 2 days.

<Diphosphomevalonate Decarboxylase Variant>

Next, description will be given of the diphosphomevalonate decarboxylase variant used in the above-described method for producing an olefin compound of the present invention. The "diphosphomevalonate decarboxylase" in the present invention is also referred to as MVD, and is an enzyme registered under EC number: 4.1.1.33. This enzyme is one of carboxy-lyases which catalyze the following reaction and produce isopentenyl diphosphate, ADP, phosphoric acid, and carbon dioxide from 5-diphosphomevalonic acid and ATP.

[Chem. 8]

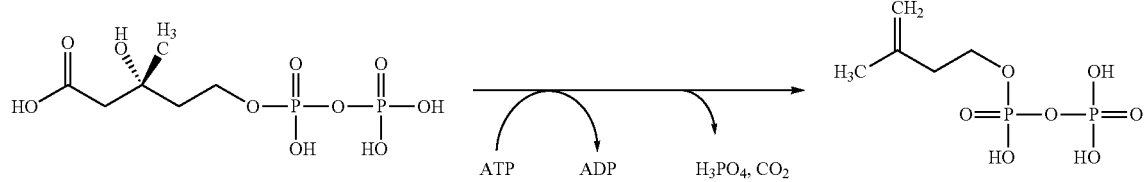

In the present invention, the diphosphomevalonate decarboxylase into which a mutation to be described later is to be introduced is not particularly limited, and those derived from various organisms can be used. Examples of such an enzyme include MVD derived from *Saccharomyces cerevisiae* (a protein comprising the amino acid sequence shown in SEQ ID NO: 2), MVD derived from *Saccharomyces cerevisiae* (strain YJM7) (a protein specifiedunderUniProt Accession No: A6ZSB7), MVD derived from *Saccharomyces cerevisiae* (strain RM11-1a) (a protein specified under UniProt Accession No: B3LPKO), MVD derived from *Candida dubliniensis* (a protein specified under UniProt Accession No: B9W6G7), MVD derived from *Pichia pastoris* (a protein specified under UniProt Accession No: C4QX63), MVD derived from *Schizosaccharomyces pombe* (a protein specified under UniProt Accession No: 0139363), MVD derived from *Ashbya gossypii* (a protein specified under UniProt Accession No: Q751D8), MVD derived from *Debaryomyces hanseni* (a protein specified under UniProt Accession No: Q6BY07), MVD derived from *Dictyostelium discoideum* (a protein specified under UniProt AccessionNo: Q54YQ9), MVD derived from *Aspergillus oryzae* (a protein specified under UniProt Accession No: Q2UGF4), MVD derived from *Encephalitozoon cuniculi* (a protein specified under UniProt Accession No: Q8SRR7), MVD derived from *Phaeodactylum tricornutum* (a protein specified under UniProt Accession No: B75422), MVD derived from Para rubber tree (*Hevea brasiliensis*) (a protein specified under UniProt Accession No: A9ZN03), MVD derived from *Nicotiana langsdorffii×Nicotiana sanderae* (a protein specified under UniProt Accession No: B3F8H5), MVD derived from *Arnebia euchroma* (a protein specified under UniProt Accession No: Q09RL4), MVD derived from *Japonica* rice (*Oryza sativa* subsp. *japonica*) (a protein specified under UniProt Accession No: Q6ETS8), MVD derived from *Arabidopsis thaliana* (a protein specified under UniProt Accession No: Q8LB37), MVD derived from tomato (*Solanum lycopersicum*) (a protein specified under UniProt Accession No: A8WBX7), MVD derived from silkworm (*Bombyx mori*) (a protein specified under UniProt Accession No: A5A7A2), MVD derived from zebrafish (*Danio rerio*) (a protein specified under UniProt Accession No: Q5U403), MVD derived from mouse (*Mus musculus*) (a protein specified under UniProt Accession No: Q99JF5 or Q3UYC1), MVD derived from brown rat (*Rattus norvegicus*) (a protein specified under UniProt Accession No: Q62967), MVD derived from cattle (*Bos taurus*) (a protein specified under UniProt Accession No: Q0P570), and MVD derived from human (*Homo sapiens*) (a protein specified under UniProt Accession No: P53602). Among these, preferable are MVDs derived from *Saccharomyces cerevisiae*, and more preferable is the protein comprising the amino acid sequence shown in SEQ ID NO: 2. Meanwhile, it should be understood that since a nucleotide sequence mutates in nature, the amino acid sequence of the protein may change.

Further, the "diphosphomevalonate decarboxylase" of the present invention may have a mutation artificially introduced therein, other than the threonine at position 209 of the amino acid sequence shown in SEQ ID NO: 2. To be more specific, the "diphosphomevalonatedecarboxylase" of the present invent ion also includes "proteins comprising amino acid sequences of diphosphomevalonate decarboxylase (such as the amino acid sequence shown in SEQ ID NO: 2) in which one or multiple amino acids are substituted, deleted, added, and/or inserted except at position 209." Here, the term "multiple" is not particularly limited, but refers to normally 1 to 80, preferably 1 to 40, more preferably 1 to 20, and further preferably 1 to 10 (for example, 1 to 8, 1 to 4, 1 to 2).

Moreover, in the "diphosphomevalonate decarboxylase" of the present invention, the position where a mutation is introduced, other than the threonine at position 209 of the amino acid sequence shown in SEQ ID NO: 2 or the threonine corresponding to the position, is not particularly limited, as long as the resultant has a catalytic activity for producing an olefin compound, Nevertheless, as described in Examples later, from the viewpoint that the activity tends to be higher, the position is preferably arginine at position 74 of the amino acid sequence shown in SEQ ID NO: 2 or arginine corresponding to the position (hereinafter, also referred to simply as "arginine at position 74").

In the present invention, the "different amino acid" mutated from the threonine at position 209 of the amino acid sequence shown in SEQ ID NO: 2 or the threonine corresponding to the position is not particularly limited. Nevertheless, as described in Examples later, from the viewpoint that a high catalytic activity is readily exhibited in the olefin compound production, preferable isarginine, asparticacid, glutamicacid, glycine, alanine, serine, or histidine.

Moreover, as described in Examples later, if the position where a mutation is introduced in the diphosphomevalonate decarboxylase is only the threonine at position 209 of the amino acid sequence shown in SEQ ID NO: 2 or the threonine corresponding to the position, preferable is histidine, serine, or arginine from the viewpoints of having a catalytic activity for producing an olefin compound and a lower substrate specificity to 5-diphosphomevalonic acid than that of a wild-type diphosphomevalonate decarboxylase. Further, from the viewpoint that the catalytic activity for producing an olefin compound is higher than that of the wild-type diphosphomevalonate decarboxylase, more preferable is histidine.

Furthermore, as described in Examples later, if the position where a mutation is introduced in the diphosphomevalonatedecarboxylase is at least the arginine at position 74 of the amino acid sequence shown in SEQ ID NO: 2 or the arginine corresponding to the position in addition to the threonine at position 209 of the amino acid sequence shown in SEQ ID NO: 2 or the threonine corresponding to the position, the different amino acid mutated from the threonine at position 209 is preferably arginine, aspartic acid, glutamic acid, glycine, or alanine, and more preferably arginine, from the viewpoint of readily having a higher catalytic activity in the olefin compound production. Further, in such a case, the different amino acid mutated from the arginine at position 74 is preferably methionine, histidine, glutamine, or lysine, and more preferably methionine or histidine.

Note that, in the present invention, a "corresponding position" and related terms refer to a position which appears in the same order as position 74 or position 209 in the amino acid sequence shown in SEQ ID NO: 2 when the amino acid sequence shown in SEQ ID NO: 2 and an amino acid sequence of MVD derived from a different strain, or the like are placed parallel to each other by utilizing nucleotide and amino acid sequence analysis software (such as GENETYX-MAC, Sequencher) or BLAST (http://blast.ncbi.nlm.nih.gov/Blast.cgi).

Meanwhile, the "wild-type diphosphomevalonate decarboxylase" is a diphosphomevalonate decarboxylase before the mutation into threonine at position 209 of the amino acid sequence shown in SEQ ID NO: 2 and the aforementioned artificial mutation are introduced. Examples of the wild type include the diphosphomevalonate decarboxylases derived from various organisms such as *Saccharomyces cerevisiae*, and naturally-occurring variants thereof.

Further, whether or not "the substrate specificity to 5-diphosphomevalonic acid" is lower than that of the wild-type diphosphomevalonate decarboxylase can be determined as described in Examples later, for example. To be more specific, the amount of free phosphoric acid formed in isopentenyl diphosphate synthesis using 5-diphosphomevalonic acid as a substrate is measured using a colorimetric detection reagent (product name: Biomol (registered trademark) Green Reagent, manufactured by Enzo Life Sciences, Inc.), and the amount is compared between the wild-type diphosphomevalonate decarboxylase and an amino acid variant thereof. Note that, regarding the substrate specificity to 5-diphosphomevalonic acid, for example, the amount of free phosphoric acid formed in the diphosphomevalonate decarboxylase variant is preferably 70% or less, more preferably 50% or less, further preferably 30% or less, furthermore preferably 10% or less, and particularly preferably 1% or less of that of the wild type.

Furthermore, whether or not the diphosphomevalonate decarboxylase variant has a catalytic activity for producing an olefin compound can be determined as described in Examples later, for example, by directly measuring the amount of an olefin compound by gas chromatography-mass spectrometry (GC-MS). Further, comparing the amount with that in the wild-type diphosphomevalonate decarboxylase makes it possible to determine whether or not the catalytic activity for producing an olefin compound is higher than that of the wild-type diphosphomevalonate decarboxylase, too.

In the present invention, the catalytic activity for producing an olefin compound of the diphosphomevalonate decarboxylase variant in comparison with that of the wild-type diphosphomevalonate decarboxylase is preferably twice or more (for example, 3 times or more, 4 times or more, 5 times or more, 6 times or more, 7 times or more, 8 times or more, 9 times or more), more preferably 10 times or more (for example, 20 times or more, 30 times or more, 40 times or more, 50 times or more), further preferably 60 times or more, furthermore preferably 70 times or more, and particularly preferably 80 times or more (for example, 90 times or more, 100 times or more).

In the present invention, as a result of the GC-MS analysis described in Examples later, the diphosphomevalonate decarboxylase variant after incubation at 37° C. for 12 hours preferably has a catalytic activity for enabling isoprene production of 0.5 mg/L or more, more preferably has a catalytic activity for enabling isoprene production of 5 mg/L or more, further preferably has a catalytic activity for enabling isoprene production of 10 mg/L or more, and furthermore preferably has a catalytic activity for enabling isoprene production of 50 mg/L or more, per mg of the enzyme.

Note that, in the present invention, the diphosphomevalonate decarboxylase variant preferably has a higher catalytic activity for producing an olefin compound than that of the wild-type diphosphomevalonate decarboxylase as described above. However, even if the activity is lower than that of the wild type, the diphosphomevalonate decarboxylase variant has a decreased activity on the original substrate 5-diphosphomevalonic acid in the biosynthesis of an olefin compound as will be described in Examples later; consequently, the amount of the olefin compound produced can be larger than that of the wild type.

Further, to the diphosphomevalonate decarboxylase variant, another compound may be added directly or indirectly. This addition is not particularly limited, and the compound may be added at a gene level, or may be chemically added. Moreover, the site of the addition is not particularly limited, either. The site may be anyone or both of an amino terminus (hereinafter also referred to as "N-terminus") and a carboxyl terminus (hereinafter also referred to as "C-terminus") of the diphosphomevalonate decarboxylase variant. The addition at a gene level is accomplished by using a DNA encoding the diphosphomevalonate decarboxylase variant to which a DNA encoding another protein is added as well as the reading frame. The "another protein" added in this manner is not particularly limited. To facilitate the purification of the diphosphomevalonate decarboxylase variant, a tag protein for purification is suitably used such as a polyhistidine (His-) tag protein, a FLAG-tag protein (registered trademark, Sigma-Aldrich Co.), or glutathione-S-transferase (GST). Moreover, to facilitate the detection of the diphosphomevalonate decarboxylase variant, a tag protein for detection is suitably used such as a fluorescent protein including GFP or a chemiluminescent protein including luciferase. The chemical addition may be covalent bonding, or may be non-covalent bonding. The "covalent bonding" is not particularly limited, and examples thereof include an amide bond between an amino group and a carboxyl group, an alkylamine bond between an amino group and an alkyl halide group, a disulfide bond between thiols, and a thioether bond between a thiol group and a maleimide group or an alkyl halide group. An example of the "non-covalent bonding" includes a binding between biotin and avidin. Further, as the "another compound" chemically added as described above, for example, a fluorescent dye such as Cy3 or rhodamine is suitably used to facilitate the detection of the diphosphomevalonate decarboxylase variant.

In addition, the diphosphomevalonate decarboxylase variant of the present invention may be used in mixture with other components. The other components are not particularly limited, and examples thereof include sterile water, a saline, a vegetable oil, a surfactant, a lipid, a solubilizer, a buffer, a protease inhibitor, and a preservative.

<DNA Encoding Diphosphomevalonate Decarboxylase Variant, and Vector Having the DNA>

Next, a DNA encoding the diphosphomevalonate decarboxylase variant, and so forth will be described. As will be described in Examples later, introducing such a DNA to transform the host cell makes it possible to produce the diphosphomevalonate decarboxylase variant in the cell, consequently producing an olefin compound.

The DNA of the present invention may be a naturally-occurring DNA in which a mutation is artificially introduced, may be a DNA comprising an artificially designed nucleotide sequence. Further, the form is not particularly limited, and includes, besides a cDNA, a genomic DNA, and a chemically synthesized DNA. These DNAs can be prepared by utilizing conventional means for those skilled in the art. The genomic DNA can be prepared, for example, by extracting a genomic DNA from *Saccharomyces cerevisiae* or the like, constructing a genomic library (as the vector, a plasmid, phage, cosmid, BAC, PAC, or the like can be utilized), deploying the library, followed by colony hybridization or plaque hybridization using a probe prepared based on the nucleotide sequence of the diphosphomevalonate decarboxylase gene (for example, the nucleotide sequence shown in SEQ ID NO: 1). Alternatively, the genomic DNA can also be prepared by producing a primer specific to the diphosphomevalonate decarboxylase gene, followed by PCR utilizing the primer. Meanwhile, the cDNA can be prepared, for example, by synthesizing a cDNA based on an mRNA extracted from *Saccharomyces cerevisiae*, inserting the cDNA into a vector such as λZAP to construct a cDNA library, deploying the library, followed by PCR or colony hybridization or plaque hybridization in the same manner as above.

Those skilled in the art can then introduce a mutation into the thus prepared DNA in such a manner that the threonine at position 209 of the amino acid sequence shown in SEQ ID NO: 2 in the diphosphomevalonate decarboxylase is substituted with a different amino acid by utilizing known methods of site-directed mutagenesis. Examples of site-directed mutagenesis include the Kunkel method (Kunkel, T. A., Proc Natl Acad Sci USA, 1985, vol. 82, no. 2, pp. 488 to 492), and SOE (splicing-by-overlap-extention)—PCR (Ho, S. N., Hunt, H. D., Horton, R. M., Pullen, J. K., and Pease, L. R., Gene, 1989, vol. 77, pp. 51 to 59).

Moreover, those skilled in the art can also chemically synthesize the DNA of the present invention by using an automatic nucleic acid synthesizer based on the sequence information of an artificially-designed nucleotide sequence encoding a diphosphomevalonate decarboxylase protein whose threonine at position 209 is substituted with a different amino acid.

It is a matter of course that, according to these methods, a different amino acid can be artificially substituted for not only the threonine at position 209 in the diphosphomevalonate decarboxylase but also arginine (for example, arginine at position 74 of the amino acid sequence shown in SEQ ID NO: 2).

Further, from the viewpoint of further enhancing the efficiency of expressing the diphosphomevalonate decarboxylase variant encoded in the host cell to be described later, the DNA of the present invention can also be in the form of a DNA encoding a diphosphomevalonate decarboxylase variant and having codons optimized in accordance with the type of the host cell.

Additionally, the present invention also provides a vector comprising the above-described DNA inserted therein so that the DNA can be replicated in the host cell.

In the present invention, the "vector" can be constructed based on a self-replicating vector, this is, for example, a plasmid which exists as an extrachromosomal element, and which replicates independently of the replication of the chromosome. Alternatively, the vector may be replicated together with the chromosome of the host cell, after introduced into the host cell and incorporated into the genome thereof.

Examples of such a vector include plasmids and phage DNAs. Moreover, the plasmids include *Escherichia coli*-derived plasmids (such as pBR322, pBR325, pUC118, pUC119, pUC18, pUC19), yeast-derived plasmids (such as YEp13, YEp24, YCp50), and *Bacillus subtilis*-derived plasmids (such as pUB110, pTP5). The phage DNAs include lambda phages (such as Charon4A, Charon21A, EMBL3, EMBL4, λgt10, λgt11, λZAP). Further, if the host cell is derived from an insect, insect viral vectors such as Baculoviridae can be used as the vector of the present invention. If the host cell is derived from a plant, T-DNA and the like can be used. If the host cell is derived from an animal, animal viral vectors such as retroviruses and adenoviral vectors can also be used. Further, as the procedure and the method for constructing the vector of the present invention, those conventionally employed in the field of genetic engineering can be employed. For example, to insert the DNA of the present invention into the vector, adopted is a method in which the purified DNA is first cleaved with an appropriate restriction enzyme, inserted into a restriction site or multiple cloning site of an appropriate vector, and linked to the vector, or other similar methods.

Moreover, the vector of the present invention may be in the form of an expression vector comprising the DNA encoding the diphosphomevalonate decarboxylase variant which can be expressed in the host cell. To introduce the "expression vector" according to the present invention into the host cell and express the diphosphomevalonate decarboxylase variant therein, the "expression vector" desirably comprises, in addition to the DNA, a DNA sequence for regulating the expression, a gene marker for selecting the transformed host cell, and the like. The DNA sequence for regulating the expression includes a promoter, an enhancer, a splicing signal, a poly-A addition signal, a ribosome binding sequence (SD sequence), a terminator, and the like. The promoter is not particularly limited, as long as the transcriptional activity is exhibited in the host cell. The promoter can be obtained as a DNA sequence for regulating the expression of a gene encoding a protein which is either homologous or heterologous to the host cell. Additionally, the "expression vector" may comprise a DNA sequence for inducing the expression, other than the DNA sequence for regulating the expression. The DNA sequence for inducing the expression includes, in a case where the host cell is a bacterium, a lactose operon capable of inducing the expression of a gene, which is located downstream, by addition of isopropyl-β-D-thiogalactopyranoside (IPTG). In the present invention, the gene marker may be selected as appropriate in accordance with the method for selecting the transformed host cell. For example, it is possible to utilize a gene encoding drug resistance, or a gene complementing the auxotrophy.

Further, the DNA or the vector of the present invention may be used in mixture with other components. The other components are not particularly limited, and examples thereof include sterile water, a saline, a vegetable oil, a surfactant, a lipid, a solubilizer, a buffer, a DNase inhibitor, and a preservative.

<Agent for Promoting Olefin Compound Production>

As described above, the use of the diphosphomevalonate decarboxylase variant, the DNA encoding the variant, or the vector comprising the DNA inserted therein makes it possible to promote olefin compound production by reacting ATP and a compound represented by the following formula (1). Thus, the present invention also provides an agent for promoting olefin compound production by reacting ATP and a compound represented by the following formula (1), the agent comprising a diphosphomevalonate decarboxylase in which at least threonine at position 209 of an amino acid sequence shown in SEQ ID NO: 2 or threonine corresponding to the position is mutated to a different amino acid, a DNA encoding the diphosphomevalonate decarboxylase, or a vector comprising the DNA inserted therein

[Chem. 9]

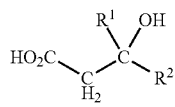

(1)

[in the formula (1), $R^1$ and $R^2$ each independently represent a hydrogen atom, an alkyl group having 1 to 10 carbon atoms, an alkenyl group having 2 to 15 carbon atoms, an aryl group having 6 to 20 carbon atoms, or a halogen atom (the alkyl group and the alkenyl group may be each independently optionally substituted with a hydroxy group and/or a carboxy group)].

Such an agent should comprise the above-described diphosphomevalonate decarboxylase variant or the like, and may be used in mixture with other components. The other components are not particularly limited, and examples thereof include sterile water, a saline, a vegetable oil, a surfactant, a lipid, a solubilizer, a buffer, a protease inhibitor, a DNase inhibitor, and a preservative.

In addition, the present invention can also provide a kit comprising such an agent. The kit of the present invention may comprise the agent in the form of a host cell which is transformed to comprise the DNA or the like of the present invention introduced therein as will be described later. Further, other than such an agent, the kit of the present invention may comprise the compound represented by the formula (1), a host cell for introducing the DNA or the like of the present invention, a medium for culturing the host cell, an instruction therefor, and so forth. Moreover, the instruction is an instruction for utilizing the agent of the present invention and so forth in the above-described method for producing an olefin compound. The instruction may comprise, for example, experimental techniques and experimental conditions for the production methods of the present invention, and information on the agent of the present invention and so forth (for example, information such as a vector map indicating the nucleotide sequence and the like of the vector, sequence information of the diphosphomevalonate decarboxylase variant, information on the origin and nature of the host cell, culturing conditions of the host cell, and so forth).

<Host Cell Comprising DNA Encoding Diphosphomevalonate Decarboxylase Variant, Etc.>

Next, the host cell comprising the DNA or the vector of the present invention will be described. As will be described in Examples later, the use of the host cell transformed by introducing the aforementioned DNA or vector therein makes it possible to produce the diphosphomevalonate decarboxylase variant, and consequently makes it possible to produce an olefin compound, as well.

The host cell into which the DNA or the vector of the present invention is to be introduced is not particularly limited, and examples thereof include microorganisms (such as *Escherichia coli, Saccharomyces cerevisiae, Schizosaccharomyces pombe, Bacillus subtilis*, actinobacteria, filamentous fungi), plant cells, insect cells, and animal cells. From the viewpoints of a high proliferation exhibited in a short time on a relatively inexpensive medium and consequent contribution to olefin compound production with a high productivity, microorganisms are preferably utilized as the host cell, and *Escherichia coli* is more preferably utilized.

In addition, the DNA or the vector of the present invention can be introduced according to methods conventionally employed in this field. Examples of the introduction methods into microorganisms such as *Escherichia coli* include a heat shock method, an electroporation method, a spheroplast method, and a lithium acetate method. The introduction methods into plant cells include a method using Agrobacterium and a particle gun method. The introduction methods into insect cells include a method using Baculoviridae and an electroporation method. The introduction methods into animal cells include a calcium phosphate method, a lipofection method, and an electroporation method.

The DNA or the like introduced in the host cell as described above may be retained in the host cell by being randomly inserted in the genomic DNA, or may be retained by homologous recombination. Meanwhile, in the case of the vector, it can be replicated and retained as an extragenomic DNA element.

<Method for Producing Diphosphomevalonate Decarboxylase Variant>

As will be described in Examples later, culturing a host cell comprising the DNA or the like of the present invention introduced therein makes it possible to produce a diphosphomevalonate decarboxylase variant in the host cell. Thus, the present invention can also provide a method for producing a diphosphomevalonate decarboxylase variant, the method comprising the steps of:

culturing the host cell; and collecting a protein expressed in the host cell.

In the present invention, the conditions for "culturing the host cell" should be conditions under which the host cell can produce the diphosphomevalonate decarboxylase variant.

Those skilled in the art can adjust and set the temperature, whether to add air or not, oxygen concentration, carbon dioxide concentration, pH of the medium, culturing temperature, culturing time, humidity, and so forth as appropriate in accordance with the type of the host cell, the medium used, and the like.

The medium should contain what the host cell can assimilate. Examples of the content include a carbon source, a nitrogen source, a sulfur source, minerals, metals, peptones, yeast extract, meat extract, casein hydrolysate, serum, and the like. Moreover, such a medium may be supplemented with, for example, IPTG for inducing the expression of the DNA encoding the diphosphomevalonate decarboxylase variant, an antibiotic (for example, ampicillin) corresponding to the drug resistance gene which can be encoded by the vector according to the present invention, or a nutrient (for example, arginine, histidine) corresponding to the gene complementing the auxotrophy which can be encoded by the vector according to the present invention.

Moreover, examples of the method for "collecting a protein expressed in the cells" from the host cell cultured as described above include methods involving: recovering the host cell from the medium by filtration, centrifugation, or the like; subjecting the recovered host cell to a treatment such as cytolysis, grinding, or pressurization crushing; and further purifying and concentrating a protein expressed in the host cell by solvent precipitation such as ultrafiltration treatment, salting-out, or ammonium sulfate precipitation, chromatography (for example, gel chromatography, ion exchange chromatography, affinity chromatography), or the like. Further, in the case where the aforementioned purification tag protein is added to the diphosphomevalonate decarboxylase variant, the purification and collection are also possible using the substrate to which the tag protein is adsorbed. Furthermore, these purification and concentration methods may be performed alone, or may be performed in an appropriate combination in multiple stages.

Alternatively, the diphosphomevalonate decarboxylase variant can also be produced by using the DNA or the like of the present invention and a cell-free protein synthesis system without limitation to the above biological synthesis. The cell-free protein synthesis system is not particularly limited, and examples thereof include synthesis systems derived from wheat germ, *Escherichia coli*, rabbit reticulocyte, or insect cells. Further, those skilled in the art can also chemically synthesize the diphosphomevalonate decarboxylase variant by using a commercially-available peptide synthesizer or the like.

Moreover, the present invention can also provide a method for producing a diphosphomevalonate decarboxylase having an enhanced catalytic activity for producing an olefin compound, the method comprising the step of mutating at least threonine at position 209 of an amino acid sequence shown in SEQ ID NO: 2 or threonine corresponding to the position in a diphosphomevalonate decarboxylase to a different amino acid.

The "diphosphomevalonate decarboxylase having an enhanced catalytic activity for producing an olefin compound" means a diphosphomevalonate decarboxylase having a higher catalytic activity for producing an olefin compound as a result of introducing a mutation into the threonine at position 209 or the like, than before the introduction. The comparison target is normally the diphosphomevalonate decarboxylases derived from various organisms such as *Saccharomyces cerevisiae*, and naturally-occurring variants thereof.

The "mutation to a different amino acid" in the diphosphomevalonate decarboxylase can be introduced by modifying the encoding DNA. Regarding the "DNA modification," such DNA modification can be performed as appropriate by employing methods known to those skilled in the art as described above, for example, site-directed mutagenesis and DNA chemical synthesis method based on modified sequence information. Moreover, the "mutation to a different amino acid" can also be introduced by employing the peptide chemical synthesis method as described above. Further, whether or not the catalytic activity for producing an olefin compound is enhanced by such mutation introduction can be evaluated by the GC-MS analysis or the like as described above.

EXAMPLES

<Preparation and Evaluation 1 of Diphosphomevalonate Decarboxylase Variants>

To achieve olefin compound production with a high productivity, the present inventors arrived at the productions of isoprene and the like via a reaction as represented by the following equation, by introducing a mutation into an amino acid of diphosphomevalonate decarboxylase (hereinafter also referred to as "MVD"), and changing the substrate specificity of the enzyme (diphosphomevalonate decarboxylase variant) from the original 5-diphosphomevalonic acid to 3-hydroxy-3-methylpent-4-enotate or the like.

[Chem. 10]

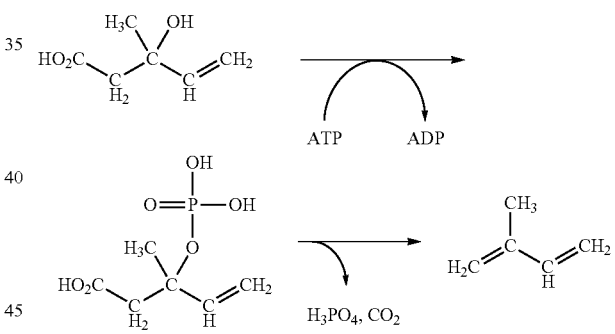

Accordingly, the present inventors adopted the following methods and so on to introduce a mutation involving amino acid substitution into various sites of diphosphomevalonate decarboxylase, and prepared a large number of diphosphomevalonate decarboxylase variants. Next, these variants were evaluated for the catalytic activity related to isopentenyl diphosphate production using 5-diphosphomevalonic acid as a substrate, and the catalytic activity related to isoprene production using 3-hydroxy-3-methylpent-4-enotate as a substrate.

<Preparation of Plasmid Vector>

First, in order to efficiently express *Saccharomyces cerevisiae*-derived MVD (scMVD, a protein comprising the amino acid sequence shown in SEQ ID NO: 2) in *Escherichia coli*, a wild-type nucleotide sequence (the nucleotide sequence shown in SEQ ID NO: 1) encoding the MVD was modified by taking the codon use frequency of *Escherichia coli* into consideration. Then, a DNA comprising the modified nucleotide sequence (the nucleotide sequence shown in SEQ ID NO: 3) was chemically synthesized according to a conventional method. Subsequently, the DNA thus prepared was inserted into a multiple cloning site (between NdeI and BamHI recognition sites) of pET-22b(+) vector (manufactured by Novagen Inc.). Thus, a plasmid vector (scMVD vector) was prepared which was capable of expressing the wild-type scMVD in *Escherichia coli*, the wild-type scMVD having a polyhistidine tag fused to the N-terminus thereof.

Next, to introduce a mutation involving amino acid substitution into each position of the scMVD as shown in Table 1 below, primers encoding amino acid sequences having mutations introduced therein were designed and synthesized.

TABLE 1

| Amino acid position | Amino acid to be substituted | Amino acid after substitution |
|---|---|---|
| 19 | Y | A, N, Q, K, R, H, D, E |
| 22 | K | F, W, Y, R |
| 28 | N | L, F, W, M, Y, Q, K, R, H, E |
| 46 | T | N, D, V, S, C |
| 48 | T | N, D, S, C |
| 61 | L | N, D, I, M, Q, E |
| 63 | L | D, N, I, M, Q, E |
| 71 | D | E, N, Q, T |
| 74 | R | H, K Y, F, W |
| 75 | T | L, I, N, D |
| 84 | Q | N, D, S, C |
| 108 | S | T, C, N, D |
| 110 | N | D, L, I, Q, E, M |
| 119 | A | G, S, C |
| 120 | S | C, T |
| 121 | S | C, T |
| 122 | A | S, C, G |
| 123 | A | G, S, C |
| 125 | F | Y, W, R, K |
| 153 | S | L, M, Y, N, D, E, A, T, C |
| 154 | G | A, V, P, S, T, C, D, N |
| 155 | S | A, T, N, C, D |
| 158 | R | Y, S, T, C, N, Q, K, H, A, E, D |
| 208 | S | H, E, N, A, Y, C, T, Q, R, D |
| 209 | T | L, F, W, M, P, I, G, V, H, N, C, S, A, Q, K, D, Y, R, E |
| 212 | M | A, Y, Q, R, E, N, K, D, H |

Then, using the scMVD vector as a template as well as these primers and a site-directed mutagenesis kit (product name: site-Direct Mutagenesis Kit, manufactured by Agilent Technologies, Inc.), plasmid vectors were prepared which were capable of expressing scMVDs in *Escherichia coli* in accordance with the protocol attached to the kit, the scMVDs each having the mutation introduced therein and the polyhistidine tag fused to the N-terminus thereof.

<Preparation of Enzyme Solution>

Each of the plasmid vectors prepared as described above was introduced into *Escherichia coli* (BL21) by a heat shock method, and transformants were prepared which were capable of expressing the wild-type scMVD or the scMVD variants. Then, each of these transformants was cultured overnight in an LB medium supplemented with 0.4 mM IPTG and ampicillin. After the culturing, the transformant was collected by centrifugation, and lysed by adding a DNase I-supplemented protein extraction reagent (product name: B-PER, manufactured by Thermo Fisher Scientific Inc.). Lysates obtained in this manner were centrifuged, and supernatants thus obtained were added to polyhistidine purification columns (product name: TALON(registered trademark) column, manufactured by Clontech Laboratories, Inc.). Then, an elution solution (20 mM Tris-HCl (pH 7.4), 300 mM NaCl, 150 mM imidazole) was added to each column to elute the scMVD to which the polyhistidine tag was fused. Subsequently, each elution solution was dialyzed with a buffer (20 mM Tris-HCl (pH 7.4), 100 mM NaCl), and then concentrated with an ultrafiltration spin column (product name: Amicon Ultra, manufactured by Millipore Corporation).

Thus, an enzyme solution was prepared. Moreover, the concentration of the enzyme (the scMVD or the variants to which the polyhistidine tag was fused) in the solution prepared as described above was measured using a protein quantification kit (product name: BCA Assay Kit, manufactured by TaKaRa Bio Co.) in accordance with the protocol attached thereto.

<Enzymatic Activity Measurement 1>

Each enzymatic activity in isopentenyl diphosphate synthesis using 5-diphosphomevalonic acid as a substrate was measured as follows.

First, 25 μM (R)-mevalonic acid 5-pyrophosphate tetralithium salt (manufactured by Sigma-Aldrich Co.) and 25 μM ATP were added to a buffer (50 mM Tris-HCl (pH 7.5), 10 mM $MgCl_2$, 100 mM KCl). Thereby, an enzymatic reaction liquid was prepared.

Figure 1:
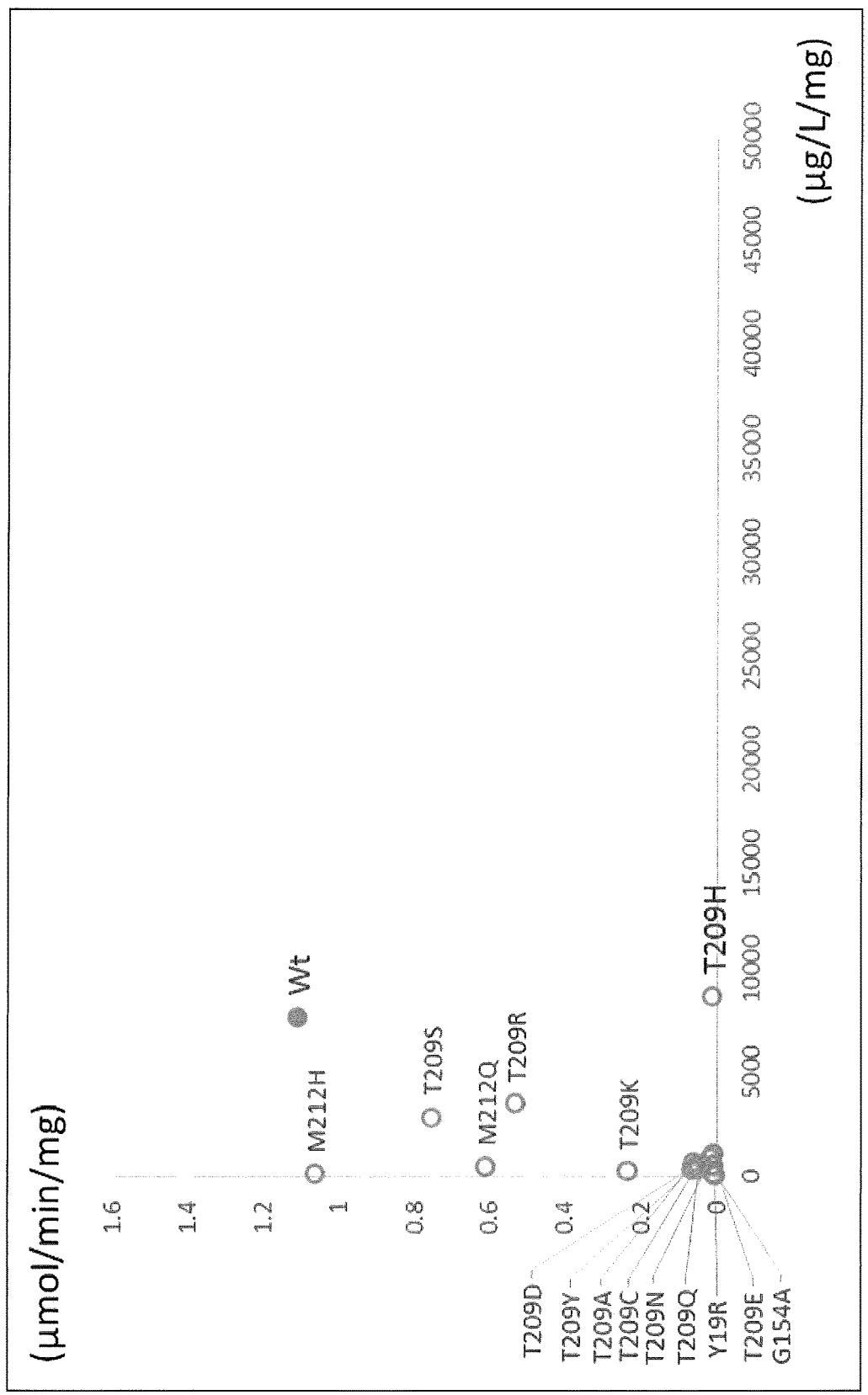
FIG. 1 is a plot showing the result of analyzing a diphosphomevalonate decarboxylase (in the drawing, indicated by "Wt") and variants thereof for the enzymatic activity related to isopentenyl diphosphate production using 5-diphosphomevalonic acid as a substrate (in the drawing, shown on the vertical axis) and the enzymatic activity related to isoprene production using 3-hydroxy-3-methylpent-4-enotate as a substrate (in the drawing, shown on the horizontal axis). Note that, in the drawing, "T209H" and the like represent the diphosphomevalonate decarboxylase variants; the numbers therein each represent a position (such as position 209) of the enzyme where a mutation involving amino acid substitution was introduced; an alphabet at the left side of the number represents an amino acid (such as T/threonine) before the substitution; and an alphabet at the right side of the number represents an amino acid (such as H/histidine) after the substitution.

After this reaction liquid was incubated at 37° C., the enzyme solution (enzyme content: 50 to 100 ng) prepared above was added to 100 μL of the reaction liquid to start the enzymatic reaction. Then, 3 minutes after the reaction was started, the amount of free phosphoric acid in the enzymatic reaction liquid was measured to calculate the enzymatic activity. Note that the amount of free phosphoric acid was measured by adding a colorimetric detection reagent (product name: Biomol(registered trademark) Green Reagent, manufactured by Enzo Life Sciences, Inc.) in the same amount to the enzymatic reaction liquid, allowing the reaction to take place at room temperature for 20 minutes, and then measuring the absorbance at a wavelength of 620 nm. Further, based on the amount of free phosphoric acid (unit: μmol) measured in this manner, the amount of the reaction product produced per mg of each enzyme in one minute was calculated as the enzymatic activity. FIG. 1 shows some of the obtained result on the vertical axis.

<Enzymatic Activity Measurement 2>

Each enzymatic activity in isoprene synthesis using 3-hydroxy-3-methylpent-4-enotate as a substrate was measured as follows.

First, 0.5 mM 3-hydroxy-3-methylpent-4-enotate (Catalog No: EN300-181938, 3-hydroxy-3-methylpent-4-enoic acid, manufactured by Enamine Building Blocks) and 5 mM ATP were added to a buffer (50 mM Tris-HCl (pH 7.5), 10 mM $MgCl_2$, 100 mM KCl).

Note that, although not conducted in this Example, in order to enable ADP formed in isoprene synthesis to be detected as an enzymatic activity through an oxidation of NADH also, 0.4 mM NADH, 1 mM phosphoenolpyruvic acid, 3 U/ml lactate dehydrogenase, and 1.5 U/ml pyruvate kinase were further added. Thereby, an enzymatic reaction liquid was prepared. To be more specific, with this enzymatic reaction liquid, first, pyruvic acid and ATP are produced by pyruvate kinase using ADP formed in isoprene synthesis and phosphoenolpyruvic acid as substrates. Further, using pyruvic acid thus formed and NADH as substrates, lactic acid and NAD+ are produced by lactate dehydrogenase. Hence, measuring a decrease in the absorbance of NADH at a wavelength of 340 nm also enables the detection of the enzymatic activity.

Then, 2.5 ml of this reaction liquid and 10 mg of the enzyme were added to a 10-ml vial for gas chromatography-mass spectrometry (GC-MS). Immediately thereafter, the vial was capped, and the enzymatic reaction was started. The enzymatic reaction was allowed to proceed at 37° C. Several days (approximately 2 days later) after the reaction was started, the amount of isoprene produced in the head space of the vial was measured by GC-MS (product name: GCMS-QP2010 Ultra, manufactured by Shimadzu Corporation). Based on the obtained measurement value, the amount of the reaction product (unit: μg/L) produced per mg of each enzyme was calculated as the enzymatic activity. FIG. 1 shows some of the obtained result on the horizontal axis.

<Measurement of Isoprene Amount in *Escherichia coli* Culture Liquid>

Figure 2:
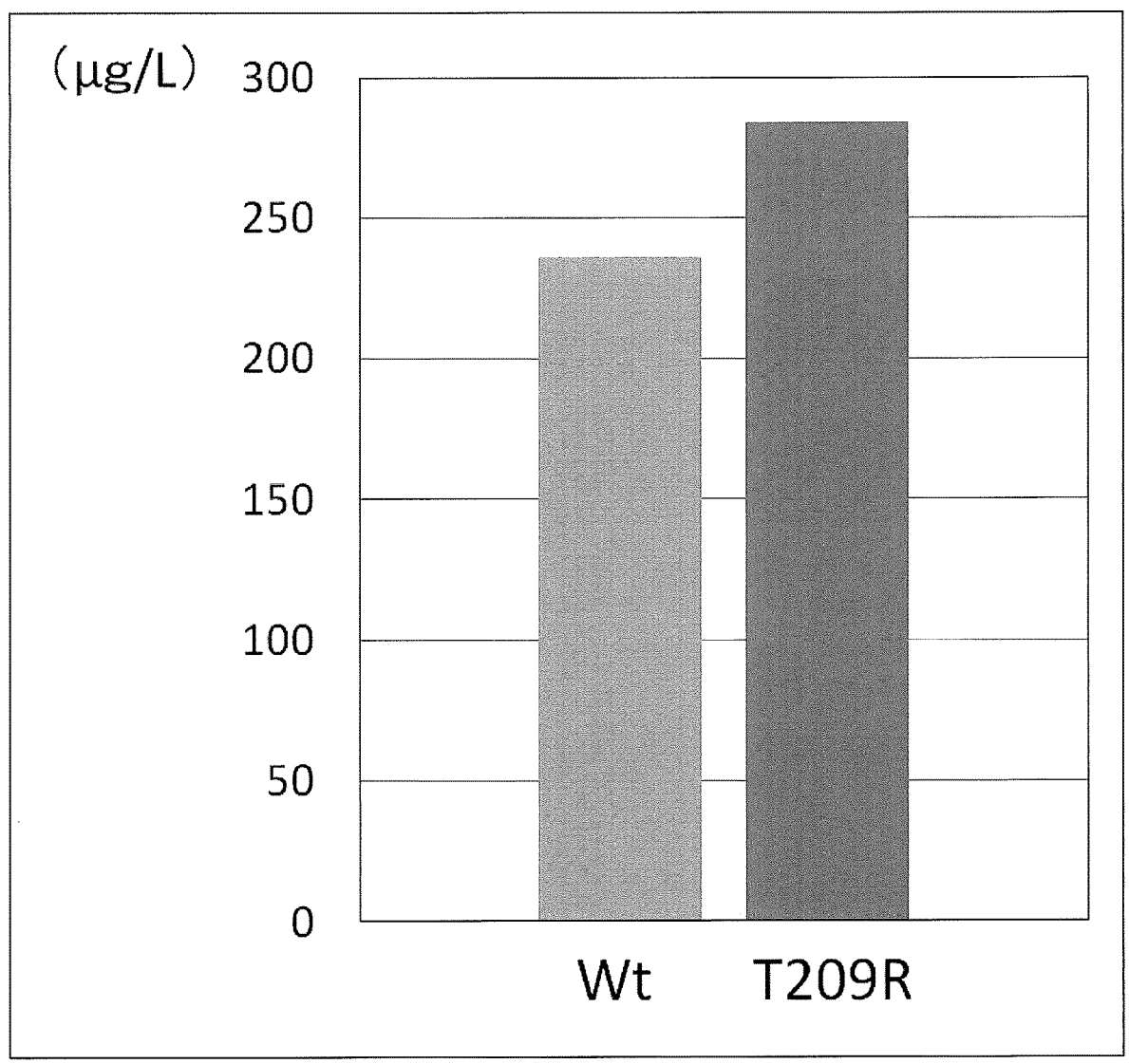
FIG. 2 is a graph showing the result of measuring the amounts of isoprene produced by culturing: Escherichia coli which was forced to express a diphosphomevalonate decarboxylase (in the drawing, indicated by "Wt"); and Escherichia coli which was forced to express a diphosphomevalonate decarboxylase whose threonine at position 209 was substituted with arginine (in the drawing, indicated by "T209R").

The transformant expressing the diphosphomevalonate decarboxylase enzyme (hereinafter also referred to as "T209R") whose threonine at position 209 was substituted with arginine was cultured in an ampicillin-supplemented LB medium at 37° C. Then, 2.5 ml of the culture liquid whose OD at a wavelength of 600 nm reached 0.4 to 0.6 was transferred to a 10-ml vial for GC-MS. IPTG was added there such that the final concentration was 0.4 mM, and further 3-hydroxy-3-methylpent-4-enotate was added such that the final concentration was 0.5 mM. The vial was capped for the culturing at 25° C. Several days (approximately 2 days later) after the culturing and the reaction were started, the amount of isoprene in the head space of the vial was directly measured by GC-MS. FIG. 2 shows the obtained result.

As is apparent from the result shown in FIG. 1, it was revealed that introducing the mutations into the diphosphomevalonate decarboxylase generally reduced the substrate specificities to 5-diphosphomevalonic acid thereof in comparison with that of the wild type. Further, it was found that the diphosphomevalonate decarboxylase enzymes (diphosphomevalonate decarboxylase variants) whose threonine at position 209 was substituted with a different amino acid (such as serine, arginine, histidine) had the catalytic activity related to isoprene production.

In addition, as shown in FIG. 1, T209R had a lower catalytic activity related to isoprene production per se than the wild type. However, as shown in FIG. 2, the amount of isoprene produced from *Escherichia coli* expressing T209R was larger than that of the wild type, possibly reflecting the low substrate specificity to 5-diphosphomevalonic acid shown in FIG. 1.

To be more specific, although it is not exactly clear why such results were obtained, the following is conceivable. Regarding the wild-type diphosphomevalonate decarboxylase, the substrates (5-diphosphomevalonic acid and 3-hydroxy-3-methylpent-4-enotate) compete with each other for the incorporation into the enzyme. Meanwhile, the incorporation of 5-diphosphomevalonic acid by T209R was reduced, so that the competition was suppressed. Thus, a larger amount of 3-hydroxy-3-methylpent-4-enotate was incorporated as the substrate into this enzyme. In addition, it can be speculated consequently that even though T209R had a lower catalytic activity related to isoprene production per se than that of the wild type, the amount of isoprene produced by *Escherichia coli* was larger than that of the wild type.

<Preparation and Evaluation 2 of Diphosphomevalonate Decarboxylase Variants>

Diphosphomevalonate decarboxylase variants shown in the following Tables 2 and 3 were additionally prepared by the methods described above in <Preparation of Plasmid Vector> and <Preparation of Enzyme Solution>, and analyzed by the method described above in <Enzymatic Activity Measurement 1>. FIGS. 3A and B show some of the obtained result on the vertical axes.

TABLE 2

| Y19A | T48D | N110D | S153A | S155A | T209A | Y19AN28A |
|------|------|-------|-------|-------|-------|----------|
| Y19D | T48S | N110E | S153C | S155C | T209C | Y19AT209A |
| Y19E | L61D | N110I | S153D | S155D | T209D | Y19AT209V |
| Y19H | L61E | N110L | S153E | S155N | T209E | K22AT209A |
| Y19K | L61I | N110M | S153F | S155T | T209F | K22AT209V |
| Y19N | L61N | N110Q | S153I | R158A | T209G | N28AT209A |
| Y19Q | L61Q | A119C | S153K | R158C | T209H | N28AT209V |
| Y19R | L63E | A119G | S153L | R158D | T209I | R74HT209A |
| K22A | L63I | A119S | S153M | R158E | T209K | R74HT209C |
| K22F | L63M | S120C | S153N | R158H | T209N | R74HT209D |
| K22R | L63N | S120T | S153Q | R158K | T209P | R74HT209E |
| K22W | L63Q | S121C | S153T | R158N | T209Q | R74HT209G |
| K22Y | D71N | A122C | S153W | R158Q | T209R | R74HT209H |
| dR23-L27 | D71Q | A122S | S153Y | R158S | T209S | R74HT209K |
| dD24-L27 | D71T | A123C | G154A | R158T | T209V | R74HT209N |
| dT25-L27 | R74F | A123G | G154C | R158Y | T209W | R74HT209Q |

TABLE 3

| N28A | R74H | A123S | G154D | S208A | T209Y | R74HT209R |
|------|------|-------|-------|-------|-------|-----------|
| N28E | R74K | F125K | G154E | S208C | M212A | R74HT209S |
| N28F | R74W | F125R | G154F | S208D | M212D | R74HT209V |
| N28H | R74Y | F125W | G154I | S208E | M212E | R74HT209W |
| N28K | T75D | F125Y | G154K | S208H | M212H | R74HT209Y |
| N28L | T75I | I145F | G154L | S208K | M212K | R74HI145F |
| N28M | T75N | I145L | G154M | S208N | M212N | R74HI145FT209H |
| N28Q | S108C | I145V | G154N | S208Q | M212Q | R74HI145FT209R |
| N28R | S108D | I145W | G154P | S208R | M212R | R74KT209H |
| N28W | S108N |       | G154Q | S208T | M212Y | R74KT209R |
| N28Y | S108T |       | G154R | S208Y |       | I145FT209H |
| T46C |       |       | G154S |       |       | I145FT209R |
| T46D |       |       | G154T |       |       |           |
| T46N |       |       | G154V |       |       |           |
| T46S |       |       | G154W |       |       |           |
| T46V |       |       | G154Y |       |       |           |

Note that, regarding the representation in the tables, for example, "R74HI145FT209H" represents a diphosphomevalonate decarboxylase variant of scMVD whose arginine at position 74 is substituted with histidine, isoleucine at position 145 is substituted with phenylalanine, and threonine at position 209 is substituted with histidine. Additionally, for example, "dR23-L27" represents a diphosphomevalonate decarboxylase variant of scMVD whose portion from arginine at position 23 to leucine at position 27 is deleted.

Moreover, by employing the following method, the additional diphosphomevalonate decarboxylase variants shown in Tables 2 and 3 were measured for the enzymatic activity in isoprene synthesis using 3-hydroxy-3-methylpent-4-enotate as a substrate.

<Enzymatic Activity Measurement 3>

First, 0.5 mM 3-hydroxy-3-methylpent-4-enotate and 5 mM ATP were added to a buffer (50 mM Tris-HCl (pH 7.5), 10 mM $MgCl_2$, 100 mM KCl).

Then, 2.5 ml of this reaction liquid and 0.5 mg of the enzyme were added to a 10-ml vial for GC-MS. Immediately thereafter, the vial was capped, and the enzymatic reaction was started. The enzymatic reaction was allowed to proceed at 37° C. One night (12 hours) after the reaction was started, heating was performed at 50° C. for 30 minutes for the sample equilibration, and then the amount of isoprene produced in the head space of the vial was measured by GC-MS. Based on the obtained measurement value, the amount of the reaction product (unit: μg/L) produced per L of each enzymatic reaction liquid was calculated as the enzymatic activity. The horizontal axes of FIGS. 3A and B as well as FIGS. 4A and B show some of the obtained result.

Further, some of the transformants producing the additional diphosphomevalonate decarboxylase variants shown in Tables 2 and 3 were analyzed by also employing the method described above in <Measurement of Isoprene Amount in *Escherichia coli* Culture Liquid>. FIG. 5 shows the obtained result.

Furthermore, by the method described below, the scMVD and the diphosphomevalonate decarboxylase variant (hereinafter "R74HT209R") whose arginine at position 74 was substituted with histidine, and whose threonine at position 209 was further substituted with arginine, were measured for the change over time in the amount of isoprene synthesized.

<Enzymatic Activity Measurement 4>

The enzymatic reaction and the GC-MS measurement were carried out in the same manner as above in <Enzymatic Activity Measurement 3>. Nevertheless, to measure the change over time in the amount of isoprene synthesized, the vial containing the enzymatic reaction liquid was immersed in liquid nitrogen at each measurement time point for freezing to stop the enzymatic reaction. Then, after the sample equilibration treatment was performed in the same manner as above, the amount of isoprene produced in the head space of the vial was measured. FIGS. 6A and B show the obtained result.

Note that, in the drawings, from both of the scMVD ("wt" in the drawings) and R74HT209R, isoprene was detected already when the measurement was started. This is because the enzymatic reaction had proceeded by the sample equilibration treatment (at 50° C. for 30 minutes) as described above.

As is apparent from the results shown in the horizontal axes of FIGS. 3A and B, it was revealed that introducing the mutations into the diphosphomevalonate decarboxylase generally reduced the substrate specificity to 5-diphosphomevalonic acid thereof in comparison with that of the wild type.

On the other hand, the resulting amount of isoprene synthesized using 3-hydroxy-3-methylpent-4-enotate as a substrate was 1400 μg/L or less in most of the prepared variants. Meanwhile, it was revealed that only the diphosphomevalonate decarboxylase variant (R74HT209R) whose arginine at position 74 was substituted with histidine, and whose threonine at position 209 was substituted with arginine, had a conspicuously very high catalytic activity related to isoprene production (the amount of isoprene synthesized: approximately 20000 μg/L).

Further, as shown in FIG. 4B, the diphosphomevalonate decarboxylase variant (R74H1145FT209R) whose isoleucine at position 145 was additionally substituted with phenylalanine was inferior in the amount of isoprene synthesized to the variant (R74HT209R) without this substitution. Nevertheless, it was revealed that both the diphosphomevalonate decarboxylase variants whose arginine at position 74 was substituted with histidine, and whose threonine at position 209 was substituted with arginine, had very high catalytic activities related to isoprene production in comparison with the large number of the other variants.

Moreover, as shown in FIG. 5, reflecting the above-described very high catalytic activity related to isoprene production, the amount of isoprene produced from *Escherichia coli* expressing R74HT209R was remarkably larger than those produced from *Escherichia coli* expressing the other diphosphomevalonate decarboxylase variants.

Furthermore, as shown in FIGS. 6A and B, R74HT209R and the wild-type diphosphomevalonate decarboxylase were measured for the change over time in the amount of isoprene produced. As a result, reflecting the above-described very high catalytic activity related to isoprene production, the difference between the amount of isoprene produced by R74HT209R and that by the wild type became more and more remarkable as time elapsed. Moreover, at Hour 24 after the reaction was started, as a result of the measurements and comparisons 8 times, the amount of isoprene produced by R74HT209R was 60 to 80 times as large as that of the wild type in any measurement. This verified that R74HT209R had a very high catalytic activity related to isoprene production as described above.

Meanwhile, PTL 3 (International Publication No. WO2015/021045) discloses M3K (EC 2.7.1.158) as an enzyme capable of producing isoprene. Hence, the isoprene conversion ratio (amount of isoprene produced/(substrate amount and enzyme amount)) was compared. The result revealed that the conversion ratio of R74HT209R was $1.2 \times 10^3$ times as high as that of M3K, and that R74HT209R had a very high catalytic activity related to isoprene production in comparison with the known enzyme.

Note that the amount of isoprene produced by R74HT209R is approximately 70 times (60 to 80 times) as large as that of the wild type as described above. Moreover, the amount of R74HT209R used to obtain this amount of isoprene was 4.5 μM, while the substrate amount was 0.5 mM. On the other hand, according to FIG. 14 and so forth of PTL 3, the amount of isoprene produced by M3K was approximately 50 times as large as that of the wild type. Moreover, the amount of M3K used to obtain this amount of isoprene was 200 μM, while the substrate amount was 10 mM. Hence, based on these numerical values, the isoprene conversion ratio of R74HT209R was evaluated to be $1.2 \times 10^3$ times as high as that of M3K as described above.

<Enzymatic Activity Measurement 5>

Next, the present inventors verified that the above-described R74HT209R which exhibited a very high catalytic activity for isoprene production was also utilizable in the production of another olefin compound. To be more specific, each enzymatic activity in isobutene synthesis (reaction represented by the following equation) using β-hydroxyisovaleric acid as a substrate was evaluated as follows.

[Chem. 11]

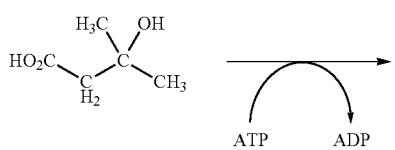

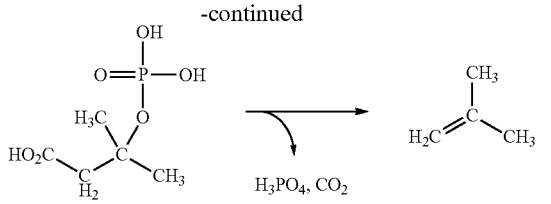

First, 0.5 mM β-hydroxylsovaleric acid (manufactured by Tokyo Chemical Industry Co., Ltd., product code: H0701) and 5 mM ATP were added to a buffer (50 mM Tris-HCl (pH 7.5), 10 mM $MgCl_2$, 100 mM KCl).

Then, 2.5 ml of this reaction liquid and 10 mg of the enzyme were added to a 10-ml vial for GC-MS. Immediately thereafter, the vial was capped, and the enzymatic reaction was started. The enzymatic reaction was allowed to proceed at 37° C. Several days (approximately 2 days later) after the reaction was started, heating was performed at 50° C. for 30 minutes for the sample equilibration, and then the amount of isobutene produced in the head space of the vial was measured by GC-MS (product name: GCMS-QP2010 Ultra, manufactured by Shimadzu Corporation). Subsequently, the area value of a peak derived from isobutene thus obtained was calculated. Note that, as a control, scMVD was used in place of R74HT209R, and the area value thereof was calculated in the same manner as above. Moreover, as a negative control, ultrapure water (milliQ water) was used in place of the enzymes, and the area value thereof was calculated in the same manner as above. Table 4 shows the obtained result.

Further, each enzymatic activity in isoprene synthesis was evaluated using 3-hydroxy-3-methylpent-4-enotate in place of β-hydroxyisovaleric acid in the same manner as above for isobutene. Table 4 shows the obtained result.

TABLE 4

| Reaction | Ultrapure water | wt | R74HT209R |
|---|---|---|---|
| (structure 1) | 2060 | 6010 | 321860 |
| (structure 2) | 3117 | 3759 | 33837 |

As is apparent from the result shown in Table 4, it was verified that R74HT209R exhibited a high catalytic activity for isobutene production, too, as in the case of the isoprene production.

<Preparation and Evaluation 3 of Diphosphomevalonate Decarboxylase Variants>

Diphosphomevalonate decarboxylase variants shown in the following Table 5 were additionally prepared by the methods described above in <Preparation of Plasmid Vector> and <Preparation of Enzyme Solution>, and analyzed by the method described above in <Enzymatic Activity Measurement 3>. Table 5 also shows the obtained result. Note that, in Table 5, the amount of isoprene produced by each diphosphomevalonate decarboxylase variant is expressed by a ratio relative to that by the wild type. In addition, in the table, "-" indicates that no mutation was introduced (position 209 was still threonine).

TABLE 5

| R74 | T209 | wt basis |
|---|---|---|
| M | D | 5.1 fold |
| M | E | 4.5 fold |
| M | G | 4.5 fold |
| M | A | 4.6 fold |
| Q | R | 6.2 fold |
| K | — | 3.8 fold |
| K | R | 2.4 fold |

As is apparent from the result shown in Table 5, it was verified that position 74 and position 209 in diphosphomevalonate decarboxylase were not limited to arginine and threonine, respectively, and that even if the amino acids were substituted with different amino acids, high catalytic activities in the catalytic reaction for isoprene production were generally exhibited in comparison with the wild type.

Further, a diphosphomevalonate decarboxylase variant (R74MT209R) whose arginine at position 74 was substituted with methionine, and whose threonine at position 209 was substituted with arginine was prepared by the methods described above in <Preparation of Plasmid Vector> and <Preparation of Enzyme Solution>. Then, R74MT209R was analyzed by the method described above in <Enzymatic Activity Measurement 3>, and the catalytic activity for isoprene production was compared with that of the above-described R74HT209R. The result also verified that R74MT209R exhibited the catalytic activity even 1.28 times as high as that of R74HT209R.

Next, these diphosphomevalonate decarboxylase variants (R74HT209R, R74MT209R) exhibiting very high catalytic activities for isoprene production were evaluated for the catalytic activity for isobutene production by the method described above in <Enzymatic Activity Measurement 5>. Table 6 shows the obtained result.

TABLE 6

| Ultrapure water | wt | R74HT209R | R74MT209R |
|---|---|---|---|
| 11232 | 63057 | 355800 | 401170 |

As is apparent from the result shown in Table 6, it was verified that R74MT209R exhibited a high catalytic activity for isobutene production, too. Moreover, it was also verified that R74MT209R had a higher catalytic activity for isobutene production than R74HT209R as in the case of the isoprene production.

INDUSTRIAL APPLICABILITY

As has been described above, the present invention makes it possible to provide an enzyme enabling olefin compound production with a high productivity, and a method for producing an olefin compound by using the enzyme. Moreover, since olefin compounds can be produced by not chemical synthesis but biosynthesis, the present invention is more environmentally friendly. Thus, the present invention is quite useful in the production of raw materials, including isoprene and isobutene, of various synthetic polymers such as synthetic rubbers.

SEQUENCE LISTING FREE TEXT

SEQ ID NO: 3
<223> Sequence codon-optimized for E. coli expression

The invention claimed is:

1. A method for producing an olefin compound, the method comprising the step of reacting ATP and a compound represented by the following formula (1) in the presence of a diphosphomevalonate decarboxylase, wherein the diphosphomevalonate decarboxylase is a protein consisting of the amino acid sequence of SEQ ID NO: 2 in which the threonine at position 209 is substituted with arginine, aspartic acid, glutamic acid, glycine, alanine, serine, or histidine, and in which 1 to 40 amino acid residues are substituted, deleted, added, and/or inserted other than at position 209,

[Chem. 1]

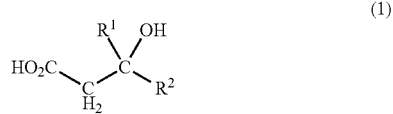

(1)

wherein in the formula (1), $R^1$ and $R^2$ each independently represent a hydrogen atom, an alkyl group having 1 to 10 carbon atoms, an alkenyl group having 2 to 15 carbon atoms, an aryl group having 6 to 20 carbon atoms, or a halogen atom and in the case of $R^1$, the alkyl group and the alkenyl group each independently optionally is substituted with carboxyl group.

2. The production method according to claim 1, wherein the reaction step is performed by culturing a host cell comprising:
   a DNA encoding the diphosphomevalonate decarboxylase, or
   a vector comprising the DNA.

3. The production method according to claim 1, wherein, in the diphosphomevalonate decarboxylase, the arginine at position 74 of the amino acid sequence shown in SEQ ID NO: 2 is mutated to a different amino acid.

4. The production method according to claim 3, wherein, in the diphosphomevalonate decarboxylase,
   the threonine at position 209 of the amino acid sequence shown in SEQ ID NO: 2 is substituted with arginine, aspartic acid, glutamic acid, glycine, or alanine, and
   the arginine at position 74 of the amino acid sequence shown in SEQ ID NO: 2 is substituted with methionine, histidine, glutamine, or lysine.

5. The production method according to claim 1, wherein the olefin compound is isoprene.

6. The production method according to claim 1, wherein the olefin compound is butadiene.

* * * * *

SEQUENCE LISTING

<160> NUMBER OF SEQ ID NOS: 3

<210> SEQ ID NO 1
<211> LENGTH: 1191
<212> TYPE: DNA
<213> ORGANISM: Saccharomyces cerevisiae
<220> FEATURE:
<221> NAME/KEY: CDS
<222> LOCATION: (1)..(1191)

<400> SEQUENCE: 1

```
atg acc gtt tac aca gca tcc gtt acc gca ccc gtc aac atc gca acc         48
Met Thr Val Tyr Thr Ala Ser Val Thr Ala Pro Val Asn Ile Ala Thr
1               5                   10                  15 ctt aag tat tgg ggg aaa agg gac acg aag ttg aat ctg ccc acc aat         96
Leu Lys Tyr Trp Gly Lys Arg Asp Thr Lys Leu Asn Leu Pro Thr Asn
                20                  25                  30 tcg tcc ata tca gtg act tta tcg caa gat gac ctc aga acg ttg acc        144
Ser Ser Ile Ser Val Thr Leu Ser Gln Asp Asp Leu Arg Thr Leu Thr
            35                  40                  45 tct gcg gct act gca cct gag ttt gaa cgc gac act ttg tgg tta aat        192
Ser Ala Ala Thr Ala Pro Glu Phe Glu Arg Asp Thr Leu Trp Leu Asn
        50                  55                  60 gga gaa cca cac agc atc gac aat gaa aga act caa aat tgt ctg cgc        240
Gly Glu Pro His Ser Ile Asp Asn Glu Arg Thr Gln Asn Cys Leu Arg
65                  70                  75                  80 gac cta cgc caa tta aga aag gaa atg gaa tcg aag gac gcc tca ttg        288
Asp Leu Arg Gln Leu Arg Lys Glu Met Glu Ser Lys Asp Ala Ser Leu
                85                  90                  95 ccc aca tta tct caa tgg aaa ctc cac att gtc tcc gaa aat aac ttt        336
Pro Thr Leu Ser Gln Trp Lys Leu His Ile Val Ser Glu Asn Asn Phe
                100                 105                 110 cct aca gca gct ggt tta gct tcc tcc gct gct ggc ttt gct gca ttg        384
Pro Thr Ala Ala Gly Leu Ala Ser Ser Ala Ala Gly Phe Ala Ala Leu
            115                 120                 125 gtc tct gca att gct aag tta tac caa tta cca cag tca act tca gaa        432
Val Ser Ala Ile Ala Lys Leu Tyr Gln Leu Pro Gln Ser Thr Ser Glu
        130                 135                 140 ata tct aga ata gca aga aag ggg tct ggt tca gct tgt aga tcg ttg        480
Ile Ser Arg Ile Ala Arg Lys Gly Ser Gly Ser Ala Cys Arg Ser Leu
145                 150                 155                 160 ttt ggc gga tac gtg gcc tgg gaa atg gga aaa gct gaa gat ggt cat        528
Phe Gly Gly Tyr Val Ala Trp Glu Met Gly Lys Ala Glu Asp Gly His
                165                 170                 175 gat tcc atg gca gta caa atc gca gac agc tct gac tgg cct cag atg        576
Asp Ser Met Ala Val Gln Ile Ala Asp Ser Ser Asp Trp Pro Gln Met
                180                 185                 190 aaa gct tgt gtc cta gtt gtc agc gat att aaa aag gat gtg agt tcc        624
Lys Ala Cys Val Leu Val Val Ser Asp Ile Lys Lys Asp Val Ser Ser
            195                 200                 205 act cag ggt atg caa ttg acc gtg gca acc tcc gaa cta ttt aaa gaa        672
Thr Gln Gly Met Gln Leu Thr Val Ala Thr Ser Glu Leu Phe Lys Glu
        210                 215                 220
```

```
aga att gaa cat gtc gta cca aag aga ttt gaa gtc atg cgt aaa gcc    720
Arg Ile Glu His Val Val Pro Lys Arg Phe Glu Val Met Arg Lys Ala
225                 230                 235                 240 att gtt gaa aaa gat ttc gcc acc ttt gca aag gaa aca atg atg gat    768
Ile Val Glu Lys Asp Phe Ala Thr Phe Ala Lys Glu Thr Met Met Asp
                245                 250                 255 tcc aac tct ttc cat gcc aca tgt ttg gac tct ttc cct cca ata ttc    816
Ser Asn Ser Phe His Ala Thr Cys Leu Asp Ser Phe Pro Pro Ile Phe
            260                 265                 270 tac atg aat gac act tcc aag cgt atc atc agt tgg tgc cac acc att    864
Tyr Met Asn Asp Thr Ser Lys Arg Ile Ile Ser Trp Cys His Thr Ile
        275                 280                 285 aat cag ttt tac gga gaa aca atc gtt gca tac acg ttt gat gca ggt    912
Asn Gln Phe Tyr Gly Glu Thr Ile Val Ala Tyr Thr Phe Asp Ala Gly
    290                 295                 300 cca aat gct gtg ttg tac tac tta gct gaa aat gag tcg aaa ctc ttt    960
Pro Asn Ala Val Leu Tyr Tyr Leu Ala Glu Asn Glu Ser Lys Leu Phe
305                 310                 315                 320 gca ttt atc tat aaa ttg ttt ggc tct gtt cct gga tgg gac aag aaa   1008
Ala Phe Ile Tyr Lys Leu Phe Gly Ser Val Pro Gly Trp Asp Lys Lys
                325                 330                 335 ttt act act gag cag ctt gag gct ttc aac cat caa ttt gaa tca tct   1056
Phe Thr Thr Glu Gln Leu Glu Ala Phe Asn His Gln Phe Glu Ser Ser
            340                 345                 350 aac ttt act gca cgt gaa ttg gat ctt gag ttg caa aag gat gtt gcc   1104
Asn Phe Thr Ala Arg Glu Leu Asp Leu Glu Leu Gln Lys Asp Val Ala
        355                 360                 365 aga gtg att tta act caa gtc ggt tca ggc cca caa gaa aca aac gaa   1152
Arg Val Ile Leu Thr Gln Val Gly Ser Gly Pro Gln Glu Thr Asn Glu
    370                 375                 380 tct ttg att gac gca aag act ggt cta cca aag gaa taa                1191
Ser Leu Ile Asp Ala Lys Thr Gly Leu Pro Lys Glu
385                 390                 395

<210> SEQ ID NO 2
<211> LENGTH: 396
<212> TYPE: PRT
<213> ORGANISM: Saccharomyces cerevisiae

<400> SEQUENCE: 2

Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
                20                  25                  30

Ser Ser Ile Ser Val Thr Leu Ser Gln Asp Asp Leu Arg Thr Leu Thr
            35                  40                  45

Ser Ala Ala Thr Ala Pro Glu Phe Glu Arg Asp Thr Leu Trp Leu Asn
        50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110

Pro Thr Ala Ala Gly Leu Ala Ser Ser Ala Ala Gly Phe Ala Ala Leu
        115                 120                 125

Val Ser Ala Ile Ala Lys Leu Tyr Gln Leu Pro Gln Ser Thr Ser Glu
    130                 135                 140
```

```
Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
        195                 200                 205

Thr Gln Gly Met Gln Leu Thr Val Ala Thr Ser Glu Leu Phe Lys Glu
    210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
                260                 265                 270

Tyr Met Asn Asp Thr Ser Lys Arg Ile Ile Ser Trp Cys His Thr Ile
            275                 280                 285

Asn Gln Phe Tyr Gly Glu Thr Ile Val Ala Tyr Thr Phe Asp Ala Gly
        290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
        355                 360                 365

Arg Val Ile Leu Thr Gln Val Gly Ser Gly Pro Gln Glu Thr Asn Glu
    370                 375                 380

Ser Leu Ile Asp Ala Lys Thr Gly Leu Pro Lys Glu
385                 390                 395

<210> SEQ ID NO 3
<211> LENGTH: 1191
<212> TYPE: DNA
<213> ORGANISM: Artificial Sequence
<220> FEATURE:
<223> OTHER INFORMATION: Sequence codon-optimized for E.coli expression
<220> FEATURE:
<221> NAME/KEY: CDS
<222> LOCATION: (1)..(1191)

<400> SEQUENCE: 3 atg acc gtt tat acc gca agc gtt acc gca ccg gtt aat att gca acc     48
Met Thr Val Tyr Thr Ala Ser Val Thr Ala Pro Val Asn Ile Ala Thr
1               5                   10                  15 ctg aaa tat tgg ggt aaa cgc gat acc aaa ctg aat ctg ccg acc aat     96
Leu Lys Tyr Trp Gly Lys Arg Asp Thr Lys Leu Asn Leu Pro Thr Asn
            20                  25                  30 agc agc att agc gtt acc ctg agc cag gat gat ctg cgt acc ctg acc    144
Ser Ser Ile Ser Val Thr Leu Ser Gln Asp Asp Leu Arg Thr Leu Thr
        35                  40                  45 agc gca gca aca gca ccg gaa ttt gaa cgt gat acc ctg tgg ctg aat    192
Ser Ala Ala Thr Ala Pro Glu Phe Glu Arg Asp Thr Leu Trp Leu Asn
    50                  55                  60
```

-continued

| | | |
|---|---|---|
| ggt gaa ccg cat agc att gat aat gaa cgt acc cag aat tgt ctg cgt<br>Gly Glu Pro His Ser Ile Asp Asn Glu Arg Thr Gln Asn Cys Leu Arg<br>65                         70                   75                 80 | 240 |
| gat ctg cgc cag ctg cgt aaa gaa atg gaa agc aaa gat gca agc ctg<br>Asp Leu Arg Gln Leu Arg Lys Glu Met Glu Ser Lys Asp Ala Ser Leu<br>                   85                   90                   95 | 288 |
| ccg acc ctg agt cag tgg aaa ctg cat att gtt agc gaa aat aac ttt<br>Pro Thr Leu Ser Gln Trp Lys Leu His Ile Val Ser Glu Asn Asn Phe<br>                100                 105               110 | 336 |
| ccg acc gca gca ggt ctg gca agc agc gca gcc ggt ttt gca gca ctg<br>Pro Thr Ala Ala Gly Leu Ala Ser Ser Ala Ala Gly Phe Ala Ala Leu<br>115                       120                 125 | 384 |
| gtt agc gca att gca aaa ctg tat cag ctg ccg cag agc acc agc gaa<br>Val Ser Ala Ile Ala Lys Leu Tyr Gln Leu Pro Gln Ser Thr Ser Glu<br>         130                 135               140 | 432 |
| att agc cgt att gca cgt aaa ggt agc ggt agc gca tgt cgt agc ctg<br>Ile Ser Arg Ile Ala Arg Lys Gly Ser Gly Ser Ala Cys Arg Ser Leu<br>145                       150                 155               160 | 480 |
| ttt ggt ggt tat gtt gca tgg gaa atg ggt aaa gcc gaa gat ggt cat<br>Phe Gly Gly Tyr Val Ala Trp Glu Met Gly Lys Ala Glu Asp Gly His<br>                   165                 170               175 | 528 |
| gat agc atg gca gtt cag att gca gat agc agc gat tgg cct cag atg<br>Asp Ser Met Ala Val Gln Ile Ala Asp Ser Ser Asp Trp Pro Gln Met<br>             180                 185               190 | 576 |
| aaa gca tgt gtt ctg gtt gtg agc gat atc aaa aaa gat gtt agc agc<br>Lys Ala Cys Val Leu Val Val Ser Asp Ile Lys Lys Asp Val Ser Ser<br>195                       200                 205 | 624 |
| acc cag ggt atg cag ctg acc gtt gca acc agc gaa ctg ttt aaa gaa<br>Thr Gln Gly Met Gln Leu Thr Val Ala Thr Ser Glu Leu Phe Lys Glu<br>         210                 215               220 | 672 |
| cgt att gaa cat gtt gtg ccg aaa cgc ttt gaa gtt atg cgt aaa gcc<br>Arg Ile Glu His Val Val Pro Lys Arg Phe Glu Val Met Arg Lys Ala<br>225                       230                 235               240 | 720 |
| att gtc gaa aaa gat ttt gcc acc ttt gca aaa gaa acc atg atg gat<br>Ile Val Glu Lys Asp Phe Ala Thr Phe Ala Lys Glu Thr Met Met Asp<br>             245                 250               255 | 768 |
| agc aat agc ttt cat gca acc tgt ctg gat agc ttt ccg cct atc ttt<br>Ser Asn Ser Phe His Ala Thr Cys Leu Asp Ser Phe Pro Pro Ile Phe<br>         260                 265               270 | 816 |
| tat atg aac gat acc agc aaa cgc att atc agc tgg tgt cat acc atc<br>Tyr Met Asn Asp Thr Ser Lys Arg Ile Ile Ser Trp Cys His Thr Ile<br>275                       280                 285 | 864 |
| aat cag ttt tat ggt gaa acc att gtg gcc tat acc ttt gat gca ggt<br>Asn Gln Phe Tyr Gly Glu Thr Ile Val Ala Tyr Thr Phe Asp Ala Gly<br>         290                 295               300 | 912 |
| ccg aat gca gtt ctg tat tat ctg gca gaa aat gaa agc aaa ctg ttc<br>Pro Asn Ala Val Leu Tyr Tyr Leu Ala Glu Asn Glu Ser Lys Leu Phe<br>305                       310                 315               320 | 960 |
| gcc ttc atc tac aaa ctg ttt ggt agc gtt ccg ggt tgg gac aaa aaa<br>Ala Phe Ile Tyr Lys Leu Phe Gly Ser Val Pro Gly Trp Asp Lys Lys<br>             325                 330               335 | 1008 |
| ttc acc acc gaa cag ctg gaa gca ttt aac cat cag ttt gaa agc agc<br>Phe Thr Thr Glu Gln Leu Glu Ala Phe Asn His Gln Phe Glu Ser Ser<br>         340                 345               350 | 1056 |
| aat ttt acc gca cgt gaa ctg gat ctg gaa ctg cag aaa gat gtt gca<br>Asn Phe Thr Ala Arg Glu Leu Asp Leu Glu Leu Gln Lys Asp Val Ala<br>355                       360                 365 | 1104 |
| cgt gtt att ctg acc cag gtg ggt agc ggt ccg caa gaa acc aat gaa<br>Arg Val Ile Leu Thr Gln Val Gly Ser Gly Pro Gln Glu Thr Asn Glu<br>         370                 375               380 | 1152 |

```
agc ctg atc gat gca aaa acc ggt ctg ccg aaa gaa tga                     1191
Ser Leu Ile Asp Ala Lys Thr Gly Leu Pro Lys Glu
385                 390             395
```